US008580756B2

(12) United States Patent
Hansen et al.

(10) Patent No.: US 8,580,756 B2
(45) Date of Patent: *Nov. 12, 2013

(54) SHORT OLIGOMER ANTAGONIST COMPOUNDS FOR THE MODULATION OF TARGET MRNA

(75) Inventors: Jens Bo Rode Hansen, Charlottelund (DK); Henrik Orum, Værløse (DK); Henrik Frydenlund Hansen, Rødovre (DK); Ellen Marie Straarup, Birkerød (DK); Niels Fisker Nielsen, Kgs. Lyngby (DK); Maj Hedtjärn, København (DK)

(73) Assignee: Santaris Pharma A/S, Horsholm (DK)

( * ) Notice: Subject to any disclaimer, the term of this patent is extended or adjusted under 35 U.S.C. 154(b) by 280 days.

This patent is subject to a terminal disclaimer.

(21) Appl. No.: 12/532,532

(22) PCT Filed: Mar. 19, 2008

(86) PCT No.: PCT/EP2008/053314
§ 371 (c)(1),
(2), (4) Date: Jan. 22, 2010

(87) PCT Pub. No.: WO2008/113832
PCT Pub. Date: Sep. 25, 2008

(65) Prior Publication Data
US 2010/0210712 A1    Aug. 19, 2010

Related U.S. Application Data

(60) Provisional application No. 60/896,419, filed on Mar. 22, 2007, provisional application No. 60/969,016, filed on Aug. 30, 2007, provisional application No. 60/972,932, filed on Sep. 17, 2007, provisional application No. 60/977,409, filed on Oct. 4, 2007, provisional application No. 60/990,125, filed on Nov. 26, 2007, provisional application No. 60/992,050, filed on Dec. 3, 2007, provisional application No. 61/012,191, filed on Dec. 7, 2007, provisional application No. 61/012,185, filed on Dec. 7, 2007, provisional application No. 61/023,244, filed on Jan. 24, 2008, provisional application No. 61/023,250, filed on Jan. 24, 2008.

(30) Foreign Application Priority Data

Oct. 9, 2007  (WO) ............... PCT/EP2007/060703

(51) Int. Cl.
*C12N 15/11*   (2006.01)
*C07H 21/04*   (2006.01)
*C12N 5/00*    (2006.01)
*C12N 5/02*    (2006.01)

(52) U.S. Cl.
USPC .............. 514/44 A; 435/375; 536/24.5

(58) Field of Classification Search
None
See application file for complete search history.

(56) References Cited

U.S. PATENT DOCUMENTS

| 4,914,210 | A  | 4/1990  | Levenson et al. |
|-----------|----|---------|-----------------|
| 4,962,029 | A  | 10/1990 | Levenson et al. |
| 5,919,795 | A  | 7/1999  | Chang et al. |
| 6,030,785 | A  | 2/2000  | Katze et al. |
| 6,121,283 | A  | 9/2000  | Chang et al. |
| 6,284,458 | B1 | 9/2001  | Anderson et al. |
| 6,423,489 | B1 | 7/2002  | Anderson et al. |
| 6,433,159 | B1 | 8/2002  | Anderson et al. |
| 7,087,229 | B2 | 8/2006  | Zhao et al. |
| 2003/0215943 | A1 | 11/2003 | Crooke et al. |
| 2005/0014712 | A1* | 1/2005 | Hansen et al. ............. 514/44 |
| 2005/0069522 | A1 | 3/2005 | Colonno et al. |
| 2005/0261218 | A1* | 11/2005 | Esau et al. ............. 514/44 |
| 2006/0035212 | A1 | 2/2006 | Balakireva |
| 2006/0035858 | A1 | 2/2006 | Geary et al. |
| 2006/0040989 | A1 | 2/2006 | Meerpoel et al. |
| 2010/0197762 | A1* | 8/2010 | Swayze ............. 514/44 A |

FOREIGN PATENT DOCUMENTS

| EP | 0 699 751 A1 | 3/1996 |
|----|--------------|--------|
| EP | 1 099 442 A2 | 5/2001 |
| EP | 0 662 157 B1 | 6/2001 |
| EP | 1 222 309 B1 | 7/2005 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 02/28875 A2 | 4/2002 |
| WO | WO 02/094250 A2 | 11/2002 |
| WO | WO 03/006475 A2 | 1/2003 |

(Continued)

OTHER PUBLICATIONS

Petersen et al., LNA: a versatile tool for therapeutics and genomics, 2003, TRENDS in Biotechnology, vol. 21, pp. 74-81.*

(Continued)

*Primary Examiner* — Dana Shin
(74) *Attorney, Agent, or Firm* — Sterne, Kessler, Goldstein & Fox P.L.L.C.

(57) ABSTRACT

The invention provides LNA gapmer oligomers of between 10-20 nucleobases in length, which have a total of 1-3 phosphodiester internucleoside linkages. Such oligomers have been found to have superior bioavailability and have also been found to selectively accumulate in kidney cells.

17 Claims, 10 Drawing Sheets

(56) References Cited

FOREIGN PATENT DOCUMENTS

| WO | WO 03/011887 A2 | 2/2003 |
|---|---|---|
| WO | WO 03/085110 A2 | 10/2003 |
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2005/013901 A2 | 2/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/036916 A2 | 4/2006 |
| WO | WO 2006/050734 A1 | 5/2006 |
| WO | WO 2006/053430 A1 | 5/2006 |
| WO | WO 2006/093526 A2 | 9/2006 |
| WO | WO 2006/112872 A2 | 10/2006 |
| WO | WO 2006/113910 A2 | 10/2006 |
| WO | WO 2007/031081 A2 | 3/2007 |
| WO | WO 2007/031091 A2 | 3/2007 |
| WO | WO 2007/112753 A2 | 10/2007 |
| WO | WO 2007/112754 A2 | 10/2007 |
| WO | WO 2007/134181 A2 | 11/2007 |
| WO | WO 2008/034122 A2 | 3/2008 |
| WO | WO 2008/034123 A2 | 3/2008 |
| WO | WO 2008/061537 A2 | 5/2008 |
| WO | WO 2008/089767 A1 | 7/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |

OTHER PUBLICATIONS

Wahlestedt et al., Potent and nontoxic antisense oligonucleotides containing locked nucleic acids, 2000, PNAS, vol. 97, pp. 5633-5638.*

Grünweller et al., Comparison of different antisense strategies in mammalian cells using locked nucleic acids, 2'-O-methyl RNA, phosphorothioates and small interfering RNA, 2003, Nucleic Acids Research, vol. 31, pp. 3185-3193.*

Opalinska et al., Oxetane modified, conformationally constrained, antisense oligodeoxyribonucleotides function efficiently as gene silencing molecules, 2004, Nucleic Acids Research, vol. 32, pp. 5791-5799.*

Beaucage, L. and Iyer, R., "Advances in the Synthesis of Oligonucleotides by the Phosphoramidite Approach," *Tetrahedron* 48:2223-2311, Pergamon Press, United Kingdom (1992).

Beaucage, L. and Iyer, R., "The Synthesis of Modified Oligonucleotides by the Phosphoramidite Approach and Their Applications," *Tetrahedron* 49:6123-6194, Pergamon Press, United Kingdom (1993).

Braasch, D., et al., "Antisense inhibition of gene expression in cells by oligonucleotides incorporating locked nucleic acids: effect of mRNA target sequence and chimera design," *Nucleic Acids Res.* 30:5160-5167, Oxford University Press, United Kingdom (2002).

Christensen, U. and Pedersen, E., "Intercalating nucleic acids containing insertions of 1-O-(1-pyrenylmethyl)glycerol: stabilisation of dsDNA and discrimination of DNA over RNA," *Nucleic Acids Res.* 30:4918-4925, Oxford University Press, United Kingdom (2002).

Dass, C., "Vehicles for oligonucleotide delivery to tumours," *J. Pharm. Pharmacol.* 54:3-27, Pharmaceutical Press, United Kingdom (2002).

Davidson, N. and Shelness, G., "Apolipoprotein B: mRNA Editing, Lipoprotein Assembly, and Presecretory Degradation," *Annu. Rev. Nutr.* 20:169-193, Annual Reviews, United States (2000).

Davis, S., et al., "Improved targeting of miRNA with antisense oligonucleotides," *Nucleic Acids Res.* 34:2294-2304, Oxford University Press, United Kingdom (2006).

Deere, J., et al., "Antisense Phosphorodiamidate Morpholino Oligomer Length and Target Position Effects on Gene-Specific Inhibition in *Eschericia coli*," *Antimicrobial Agents and Chemotherapy* 49:249-255, American Society for Microbiology, United States (2005).

Elbashir, S., et al., "Analysis of gene function in somatic mammalian cells using small interfering RNAs," *Methods* 26:199-213, Academic Press, United States (2002).

Elmén, J., et al., "Locked nucleic acid containing antisense oligonucleotides enhance inhibition of HIV-1 genome dimerization and inhibit virus replication," *FEBS Letters* 578:285-290, Elsevier B.V., The Netherlands (2004).

Feld, J., et al., "Ribavirin Improves Early Response to Peginterferon Through Improved Interferon Signaling," *Gastroenterology* 139:154-162, W.B. Saunders, United States (2010).

Frieden, M., et al., "Expanding the design horizon of antisense oligonucleotides with alpha-L-LNA," *Nucleic Acids Res.* 39:6365-6372, Oxford University Press, United Kingdom (2003).

Gentleman, R., et al., "Bioconductor: open software development for computational biology and bioinformatics," *Genome Biol.* 5:R80, BioMed Central Ltd., United Kingdom (2004).

Giles, R., et al., "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Greene, T. and Wuts, P., Protective Groups in Organic Synthesis, [Table of Contents], 3rd ed., John Wiley & Sons, Chichester, England (1999).

Hanecak, R., et al., "Antisense Oligonucleotide Inhibition of Hepatitis C Virus Gene Expression in Transformed Hepatocytes," *J. Virol.* 70:5203-5212, American Society for Microbiology, United States (1996).

Heid, C., et al., "Real Time Quantitative PCR," *Genome Res.* 6:986-994, Cold Spring Harbor Laboratory Press, United States (1996).

Huber, W., et al., "Variance stabilization applied to microarray data calibration and to the quantification of differential expression," *Bioinformatics* 18:S96-S104, Oxford University Press, United Kingdom (2002).

Hutton, J., "Renaturation kinetics and thermal stability of DNA in aqueous solutions of formamide and urea," *Nucleic Acids Res.* 4:3537-3555, Oxford University Press, United Kingdom (1977).

Hutvágner, G., et al., "A Cellular Function for the RNA-Interference Enzyme Dicer in the Maturation of the *let-7* Small Temporal RNA," *Science* 293:834-838, American Assn. for the Advancement of Science, United States (2001).

Hutvágner, G., et al., "Sequence-Specific Inhibition of Small RNA Function," *PLoS Biology* 2:0465-0475, Public Library of Science, United States (2004).

Ittig, D., et al., "Nuclear antisense effects in cyclophilin A pre-mRNA splicing by oligonucleotides: a comparison of tricyclo-DNA with LNA," *Nucleic Acids Res.* 32:346-353, Oxford University Press (2004).

Johansson, H., et al., "Target-specific arrest of mRNA translation by antisense 2'-O-alkyloligonucleotides," *Nucleic Acids Res.* 22: 4591-4598, Oxford University Press, United Kingdom (1994).

Johnson, S., et al., "*RAS* is Regulated by the *let-7* MicroRNA Family," *Cell* 120:635-647, Cell Press, United States (2005).

Kauppinen, S., et al., "Locked nucleic acid (LNA): High affinity targeting of RNA for diagnostics and therapeutics," *Drug Discovery Today: Technologies* 2:287-290, Elsevier, Ltd., The Netherlands (2005).

Ketting, R., et al., "Dicer functions in RNA interference and in synthesis of small RNA involved in developmental timing in *C.elegans*," *Genes Dev.* 15:2654-2659, Cold Spring Harbor Laboratory Press, United States (2001).

Kloosterman, W., et al., "Substrate requirements for *let-7* function in the developing zebrafish embryo," *Nucleic Acids Res.* 32:6284-6291, Oxford University Press, United Kingdom (2004).

Krukemeyer, M., et al., "Description of B lymphocytes and plasma cells, complement, and chemokines/receptors in acute liver allograft rejection," *Transplantation* 78:65-70, Lippincott Williams & Wilkins, United States (2004).

(56) References Cited

OTHER PUBLICATIONS

Krützfeldt, J., et al., Specificity, duplex degradation and subcellular localization of antagomirs, *Nucleic Acids Res.* 35:2885-2892, Oxford University Press, United Kingdom (2007).

Kurreck, J., et al., "Design of antisense oligonucleotides stabilized by locked nucleic acids," *Nucleic Acids Res.* 30:1911-1918, Oxford University Press, United Kingdom (2002).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society for Microbiology, United States (2003).

Lanford, R., et al., "Lack of response to exogenous interferon-alpha in the liver of chimpanzees chronically infected with hepatitis C virus," *Hepatology* 46:999-1008, Wiley, United States (2007).

Lima, W., et al., "Combinatorial Screening and Rational Optimization for Hybridization to Folded Hepatitis C Virus RNA of Oligonucleotides with Biological Antisense Activity," *J. Biol. Chem.* 272:626-638, A237 (1997).

Lisziewicz, J., et al., "Long-term treatment of human immunodeficiency virus-infected cells with antisense oligonucleotide phosphorothioates," *Proc. Natl. Acad. Sci.* 90:3860-3864, National Academy of Sciences, United States (1993).

Manoharan, M., et al., "Novel Functionalization of the Sugar Moiety of Nucleic Acids for Multiple Labeling in the Minor Groove," *Tetrahedron Letters* 34:7171-7174, Pergamon Press, PLC., United Kingdom (1991).

Martinez, J., et al., Single-Stranded Antisense siRNAs Guide Target RNA Cleavage in RNAi, *Cell* 110:563-574, Cell Press, United States (2002).

Matz, M., et al., "Early post-transplant urinary IP-10 expression after kidney transplantation is predictive of short- and long-term graft function," *Kidney Int.* 69:1683-1690, Nature Publishing Group (2006).

McManus, M., and Sharp, P., "Gene Silencing in Mammals by Small Interfering RNAs," *Nat. Rev. Genet,* 3:737-747, Nature Publishing Group, United Kingdom (2002).

Möröy, T., et al., "Structure and expression of *hcr*, a locus rearranged with c-myc in a woodchuck hepatocellular carcinoma," *Oncogene* 4:59-65, Nature Publishing Group, United Kingdom (1989).

Neuman, B., et al., "Antisense Morpholino-Oligomers Directed against the 5' End of the Genome Inhibit Coronavirus Proliferation and Growth," *J. Virol.* 78:5891-5899, American Society for Microbiology, United States (2004).

Nulf, C. and Corey, D., "Intracellular inhibition of hepatitis C virus (HCV) internal ribosomal entry site (IRES)-dependent translation by peptide nucleic acids (PNAs) and locked nucleic acids (LNAs)," *Nucleic Acids Res.* 32:3792-3798, Oxford University Press, United Kingdom (2004).

Ørom, U., et al., "LNA-modified oligonucleotides mediate specific inhibition of microRNA function," *Gene* 372:137-141, Elsevier, Inc., The Netherlands (2006).

Paushkin, S., et al., "The SMN complex, an assemblyosome of ribonucleoproteins," *Curr. Opin. Cell Biol.* 14:305-312, Elsevier Science Ltd., United Kingdom (2002).

Pedersen, D., et al., "Preparation of LNA Phosphoramidites," *Synthesis* 6:802-808, Thieme/Academic Press, Germany (2002).

Pedersen, D., and Koch, T., "Analogues of LNA (Locked Nucleic Acid). Synthesis of the 2'Thio-LNA Thymine and 5-Methyl Cytosine Phosphoramidites," *Synthesis* 4:578-582, Thieme/Academic Press, Germany (2003).

Petri, A., et al., "MicroRNA Silencing in Primates: Towards Development of Novel Therapeutics," *Can Res.* 69:393-395, American Association for Cancer Research, United States (2009).

Prakash, T., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.* 53:1636-1650, American Chemical Society, United States (2010).

Randall, G., et al., "Cellular cofactors affecting hepatitis C virus infection and replication," *Proc. Natl. Acad. Sci. USA* 104:12884-12889, National Academy of Sciences, United States (2007).

Rosenbohm, C., et al., "Synthesis of 2'-amino-LNA: a new strategy," *Org. Biomol. Chem.* 1:655-663, Royal Society of Chemistry, United Kingdom (2003).

Saeed, A., et al., "TM4: A Free, Open-Source System for Microarray Data Management and Analysis," *BioTechniques* 34:374-378, Informa Healthcare USA, Inc., United Kingdom (2003).

Samuel, D., "Hepatitis C, Interferon, and Risk of Rejection After Liver Transplantation," *Liver Transpl.*10:868-887, Wiley InterScience, United States (2004).

Santaris Pharma, Nature Genetics Ad, Jun. 2006 [powerpoint slide], 1 page.

Sazani, P., et al., "Nuclear antisense effects of neutral, anionic and cationic oligonucleotide analogs," *Nucelic Acids. Res.* 29:3965-3974, Oxford University Press, United Kingdom (2001).

Schwarz, D., et al., "Evidence that siRNAs Function as Guides, Not Primers, in the *Drosophila* and Human RNAi Pathways," *Mol. Cell* 10:537-548, Cell Press, United States (2002).

Seth, P., et al., "Synthesis and Biophysical Evaluation of 2',4'-Constrained 2'O-Methoxyethyl and 2',4'-Constrained 2'O-Ethyl Nucleic Acid Analogues," *J. Org. Chem.* 75:1569-1581, American Chemical Society, United States (2010).

Singh, S. and Wengel, J., "Synthesis of Novel Bicyclo[2.2.1] Ribonucleosides: 2'-Amino- and 2'-Thio-LNA Monomeric Nucleosides," *J. Org. Chem.* 63:6078-6079, American Chemical Society, United States (1998).

Sørensen, M., et al.,"α-L-*ribo*-Configured Locked Nucleic Acid (α-L-LNA): Synthesis and Properties," *J. Am. Chem. Soc.* 124:2164-2176, American Chemical Society, United States (2002).

Tallet-Lopez, B., et al., "Antisense oligonucleotides targeted to the domain IIId of the hepatitis C virus IRES compete with 40S ribosomal subunit binding and prevent in vitro translation," *Nucleic Acids Res.* 31:734-742, Oxford University Press, United Kingdom (2003).

Tam, W., "Identification and characterization of human *BIC*, a gene on chromosome 21 that encodes a noncoding RNA," *Gene* 274:157-167, Elsevier, The Netherlands (2001).

Tijsterman, M., et al., "RNA Helicase MUT-14-Depedent Gene Silencing Triggered in *C.elegans* by Short Antisense RNAs," *Science* 295:694-697, American Assn. for the Advancement of Science, United States (2002).

Uhlmann, E., "Recent advances in the medicinal chemistry of antisense oligonucleotides," *Curr. Opin. Drug Discov. Develop.* 3:203-213, Pharma Press Ltd., United Kingdom (2000).

Wagner, R., "Gene inhibition using antisense oligodeoxynucleotides," *Nature* 372:333-335, Nature Publishing Group, United Kingdom (1994).

Wagner, R., et al., "Potent and selective inhibition of gene expression by an antisense heptanucleotide," *Nat. Biotechnol.* 14:840-844, Nature Publishing Group, United States (1996).

Wahlestedt, C., et al., "Potent and nontoxic antisense oligonucleotides containing locked nucleic acids," *Proc. Natl. Acad. Sci. USA* 97:5633-5638, National Academy of the Sciences, United States (2000).

Walter, T., et al., "Rejection Under Alpha Interferon Therapy in Liver Transplant Recipients," *American Journal of Transplantation* 7:177-184, Blackwell Munksgaard, Denmark (2007).

Yu, J., et al., "RNA interference by expression of short-interfering RNAs and hairpin RNAs in mammalian cells," *Proc. Natl. Acad. Sci.* 99:6047-6052, National Academy of Sciences, United States (2002).

Zhang, H., et al., "Antisense Oligonucleotide Inhibition of Hepatisis C Virus (HCV) Gene Expression in Livers of Mice Infected with an HCV-Vaccinia Virus Recombinant," *Antimicrobial Agents and Chemotherapy* 43:347-353, American Society for Microbiology, United States (1999).

Zhao, Y., et al., "Serum response factor regulates a muscle-specific microRNA that targets *Hand2* during cardiogenesis," *Nature* 436:214-220, Nature Publishing Group, United Kingdom (2005).

\* cited by examiner

SEQUENCE LISTING

```
<160> NUMBER OF SEQ ID NOS: 74

<210> SEQ ID NO 1
<211> LENGTH: 16
<212> TYPE: DNA
<213> ORGANISM: Artificial
<220> FEATURE:
<223> OTHER INFORMATION: Antisense motif

<400> SEQUENCE: 1
cagcattggt attcag                                                  16

<210> SEQ ID NO 2
<211> LENGTH: 15
<212> TYPE: DNA
<213> ORGANISM: Artificial
<220> FEATURE:
<223> OTHER INFORMATION: Antisense motif

<400> SEQUENCE: 2
cagcattggt attca                                                   15

<210> SEQ ID NO 3
<211> LENGTH: 15
<212> TYPE: DNA
<213> ORGANISM: Artificial
<220> FEATURE:
<223> OTHER INFORMATION: Antisense motif

<400> SEQUENCE: 3
agcattggta ttcag                                                   15

<210> SEQ ID NO 4
<211> LENGTH: 14
<212> TYPE: DNA
<213> ORGANISM: Artificial
<220> FEATURE:
<223> OTHER INFORMATION: Antisense motif

<400> SEQUENCE: 4
cagcattggt attc                                                    14
```

```
<210> SEQ ID NO 5
<211> LENGTH: 14
<212> TYPE: DNA
<213> ORGANISM: Artificial
<220> FEATURE:
<223> OTHER INFORMATION: Antisense motif

<400> SEQUENCE: 5
agcattggta ttca                                                   14

<210> SEQ ID NO 6
<211> LENGTH: 14
<212> TYPE: DNA
<213> ORGANISM: Artificial
<220> FEATURE:
<223> OTHER INFORMATION: Antisense motif

<400> SEQUENCE: 6
gcattggtat tcag                                                   14

<210> SEQ ID NO 7
<211> LENGTH: 13
<212> TYPE: DNA
<213> ORGANISM: Artificial
<220> FEATURE:
<223> OTHER INFORMATION: Antisense motif

<400> SEQUENCE: 7
cagcattggt att                                                    13

<210> SEQ ID NO 8
<211> LENGTH: 13
<212> TYPE: DNA
<213> ORGANISM: Artificial
<220> FEATURE:
<223> OTHER INFORMATION: Antisense motif

<400> SEQUENCE: 8
agcattggta ttc                                                    13

<210> SEQ ID NO 9
<211> LENGTH: 13
<212> TYPE: DNA
<213> ORGANISM: Artificial
<220> FEATURE:
<223> OTHER INFORMATION: Antisense motif

<400> SEQUENCE: 9
gcattggtat tca                                                    13

<210> SEQ ID NO 10
<211> LENGTH: 13
<212> TYPE: DNA
<213> ORGANISM: Artificial
<220> FEATURE:
<223> OTHER INFORMATION: Antisense motif

<400> SEQUENCE: 10
cattggtatt cag                                                    13

<210> SEQ ID NO 11
<211> LENGTH: 12
<212> TYPE: DNA
<213> ORGANISM: Artificial
<220> FEATURE:
<223> OTHER INFORMATION: Antisense motif
```

```
<400> SEQUENCE: 11
cagcattggt at                                                         12

<210> SEQ ID NO 12
<211> LENGTH: 12
<212> TYPE: DNA
<213> ORGANISM: Artificial
<220> FEATURE:
<223> OTHER INFORMATION: Antisense motif

<400> SEQUENCE: 12
agcattggta tt                                                         12

<210> SEQ ID NO 13
<211> LENGTH: 12
<212> TYPE: DNA
<213> ORGANISM: Artificial
<220> FEATURE:
<223> OTHER INFORMATION: Antisense motif

<400> SEQUENCE: 13
gcattggtat tc                                                         12

<210> SEQ ID NO 14
<211> LENGTH: 12
<212> TYPE: DNA
<213> ORGANISM: Artificial
<220> FEATURE:
<223> OTHER INFORMATION: Antisense motif

<400> SEQUENCE: 14
cattggtatt ca                                                         12

<210> SEQ ID NO 15
<211> LENGTH: 12
<212> TYPE: DNA
<213> ORGANISM: Artificial
<220> FEATURE:
<223> OTHER INFORMATION: Antisense motif

<400> SEQUENCE: 15
attggtattc ag                                                         12

<210> SEQ ID NO 16
<211> LENGTH: 15
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (13)..(15)
<223> OTHER INFORMATION: LNA units
<220> FEATURE:
<221> NAME/KEY: misc_feature
<222> LOCATION: (13)..(13)
<223> OTHER INFORMATION: 5 methyl cytosine
```

```
<400> SEQUENCE: 16
agcattggta ttcag                                                  15

<210> SEQ ID NO 17
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 17
agcattggta ttca                                                   14

<210> SEQ ID NO 18
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (2)..(14)
<223> OTHER INFORMATION: Phosphorothioate linkages
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 18
agcattggta ttca                                                   14

<210> SEQ ID NO 19
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: Phosphorothioate linkage
```

```
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(14)
<223> OTHER INFORMATION: Phosphorothioate linkage
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 19
agcattggta ttca                                                         14

<210> SEQ ID NO 20
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (4)..(14)
<223> OTHER INFORMATION: Phosphorothioate linkages
<220> FEATURE:
<221> NAME/KEY: misc_feature
<222> LOCATION: (12)..(14)
<223> OTHER INFORMATION: LNA units

<400> SEQUENCE: 20
agcattggta ttca                                                         14

<210> SEQ ID NO 21
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
```

```
<220> FEATURE:
<221> NAME/KEY: misc_feature
<222> LOCATION: (13)..(13)
<223> OTHER INFORMATION: 5 methyl cytosine

<400> SEQUENCE: 21
agcattggta ttca                                                        14

<210> SEQ ID NO 22
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (13)..(13)
<223> OTHER INFORMATION: 5 methyl cytosine

<400> SEQUENCE: 22
agcattggta ttca                                                        14

<210> SEQ ID NO 23
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (13)..(13)
<223> OTHER INFORMATION: 5 methyl cytosine

<400> SEQUENCE: 23
agcattggta ttca                                                        14
```

```
<210> SEQ ID NO 24
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (2)..(13)
<223> OTHER INFORMATION: Phosphorothioate linkages
<220> FEATURE:
<221> NAME/KEY: misc_feature
<222> LOCATION: (3)..(3)
<223> OTHER INFORMATION: 5 mthyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 24
agcattggta ttca                                                        14

<210> SEQ ID NO 25
<211> LENGTH: 14
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 25
agcattggta ttca                                                        14

<210> SEQ ID NO 26
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
```

```
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 26
gcattggtat tca                                                          13

<210> SEQ ID NO 27
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(13)
<223> OTHER INFORMATION: Phosphorothioate linkage
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 27
gcattggtat tca                                                          13

<210> SEQ ID NO 28
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(13)
<223> OTHER INFORMATION: Phosphorothioate linkage
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine
```

<400> SEQUENCE: 28
gcattggtat tca                                                              13

<210> SEQ ID NO 29
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 29
gcattggtat tca                                                              13

<210> SEQ ID NO 30
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: misc_feature
<222> LOCATION: (12)..(12)
<223> OTHER INFORMATION: 5 methyl cytosine

<400> SEQUENCE: 30
gcattggtat tca                                                              13

<210> SEQ ID NO 31
<211> LENGTH: 13
<212> TYPE: DNA
<213> ORGANISM: Artificial
<220> FEATURE:
<223> OTHER INFORMATION: LNA oligomeric compound

```
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 31
gcattggtat tca                                                      13

<210> SEQ ID NO 32
<211> LENGTH: 13
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(12)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (12)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 32
gcattggtat tca                                                      13

<210> SEQ ID NO 33
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
```

```
<220> FEATURE:
<221> NAME/KEY: misc_feature
<222> LOCATION: (12)..(12)
<223> OTHER INFORMATION: 5 methyl cytosine

<400> SEQUENCE: 33
gcattggtat tc                                                             12

<210> SEQ ID NO 34
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 34
gcattggtat tc                                                             12

<210> SEQ ID NO 35
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 35
gcattggtat tc                                                             12

<210> SEQ ID NO 36
<211> LENGTH: 12
<212> TYPE: DNA
<213> ORGANISM: Artificial
<220> FEATURE:
<223> OTHER INFORMATION: LNA oligomeric compound
```

```
<220> FEATURE:
<221> NAME/KEY: misc_feature
<222> LOCATION: (1)..(2)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 36
gcattggtat tc                                                          12

<210> SEQ ID NO 37
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 37
gcattggtat tc                                                          12

<210> SEQ ID NO 38
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
```

```
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 38
gcattggtat tc                                                            12

<210> SEQ ID NO 39
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 39
gcattggtat tc                                                            12

<210> SEQ ID NO 40
<211> LENGTH: 12
<212> TYPE: DNA
<213> ORGANISM: Artificial
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(10)
<223> OTHER INFORMATION: Phosphorothioate linkages
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 40
gcattggtat tc                                                            12

<210> SEQ ID NO 41
<211> LENGTH: 14
```

-continued

```
<212> TYPE: DNA
<213> ORGANISM: Artificial
<220> FEATURE:
<223> OTHER INFORMATION: Hif 1 alpha oligomer sequence motif

<400> SEQUENCE: 41
ggcaagcatc ctgt                                                    14

<210> SEQ ID NO 42
<211> LENGTH: 14
<212> TYPE: DNA
<213> ORGANISM: Artificial
<220> FEATURE:
<223> OTHER INFORMATION: Hif 1 alpha oligomer sequence motif

<400> SEQUENCE: 42
ggcaagcatc ctgt                                                    14

<210> SEQ ID NO 43
<211> LENGTH: 14
<212> TYPE: DNA
<213> ORGANISM: Artificial
<220> FEATURE:
<223> OTHER INFORMATION: Hif 1 alpha oligomer sequence motif

<400> SEQUENCE: 43
ggcaagcatc ctgt                                                    14

<210> SEQ ID NO 44
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 44
ggcaagcatc ctg                                                     13

<210> SEQ ID NO 45
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 45
ggcaagcatg ctg                                                     13

<210> SEQ ID NO 46
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 46
gcaagcatcc tgt                                                     13

<210> SEQ ID NO 47
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 47
gcaagcatcc tgt                                                     13
```

<210> SEQ ID NO 48
<211> LENGTH: 12
<212> TYPE: DNA
<213> ORGANISM: Artificial
<220> FEATURE:
<223> OTHER INFORMATION: Hif 1 alpha oligomer sequence motif

<400> SEQUENCE: 48
gcaagcatcc tg                                                          12

<210> SEQ ID NO 49
<211> LENGTH: 12
<212> TYPE: DNA
<213> ORGANISM: Artificial
<220> FEATURE:
<223> OTHER INFORMATION: Hif 1 alpha oligomer sequence motif

<400> SEQUENCE: 49
gcaagcatcc tg                                                          12

<210> SEQ ID NO 50
<211> LENGTH: 12
<212> TYPE: DNA
<213> ORGANISM: Artificial
<220> FEATURE:
<223> OTHER INFORMATION: Hif 1 alpha oligomer sequence motif

<400> SEQUENCE: 50
gcaagcatcc tg                                                          12

<210> SEQ ID NO 51
<211> LENGTH: 14
<212> TYPE: DNA
<213> ORGANISM: Artificial
<220> FEATURE:
<223> OTHER INFORMATION: Hif 1 alpha oligomer sequence motif

<400> SEQUENCE: 51
ggcaagcatc ctgt                                                        14

<210> SEQ ID NO 52
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 52
ggcaagcatc ctg                                                         13

<210> SEQ ID NO 53
<211> LENGTH: 13
<212> TYPE: DNA
<213> ORGANISM: Artificial
<220> FEATURE:
<223> OTHER INFORMATION: Hif 1 alpha oligomer sequence motif

<400> SEQUENCE: 53
gcaagcatcc tgt                                                         13

<210> SEQ ID NO 54
<211> LENGTH: 12
<212> TYPE: DNA
<213> ORGANISM: Artificial
<220> FEATURE:
<223> OTHER INFORMATION: Hif 1 alpha oligomer sequence motif

```
<400> SEQUENCE: 54
gcaagcatcc tg                                                              12

<210> SEQ ID NO 55
<211> LENGTH: 16
<212> TYPE: DNA
<213> ORGANISM: Artificial
<220> FEATURE:
<223> OTHER INFORMATION: Hif 1 alpha oligomer sequence motif

<400> SEQUENCE: 55
tggcaagcat cctgta                                                          16

<210> SEQ ID NO 56
<211> LENGTH: 16
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 56
tggcaagcat cctgta                                                          16

<210> SEQ ID NO 57
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (12)..(13)
<223> OTHER INFORMATION: LNA

<400> SEQUENCE: 57
ggcaagcatc ctgt                                                            14

<210> SEQ ID NO 58
<211> LENGTH: 12
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
```

```
<220> FEATURE:
<221> NAME/KEY: misc_feature
<222> LOCATION: (11)..(12)
<223> OTHER INFORMATION: LNA

<400> SEQUENCE: 58
gcaagcatcc tg                                                              12

<210> SEQ ID NO 59
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA

<400> SEQUENCE: 59
ggcaagcatc ctgt                                                            14

<210> SEQ ID NO 60
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(14)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (12)..(14)
<223> OTHER INFORMATION: LNA

<400> SEQUENCE: 60
ggcaagcatc ctgt                                                            14

<210> SEQ ID NO 61
<211> LENGTH: 13
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (12)..(13)
<223> OTHER INFORMATION: LNA
```

```
<400> SEQUENCE: 61
ggcaagcatc ctg                                                    13

<210> SEQ ID NO 62
<211> LENGTH: 13
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (11)..(11)
<223> OTHER INFORMATION: 5 methyl cytosine

<400> SEQUENCE: 62
ggcaagcatc ctg                                                    13

<210> SEQ ID NO 63
<211> LENGTH: 13
<212> TYPE: DNA
<213> ORGANISM: Artificial
<220> FEATURE:
<223> OTHER INFORMATION: LNA olgiomer
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA

<400> SEQUENCE: 63
gcaagcatcc tgt                                                    13

<210> SEQ ID NO 64
<211> LENGTH: 13
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(13)
<223> OTHER INFORMATION: Phosphorothioate linkage
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: 5 methyl cytosine
```

```
<220> FEATURE:
<221> NAME/KEY: misc_feature
<222> LOCATION: (12)..(13)
<223> OTHER INFORMATION: LNA

<400> SEQUENCE: 64
gcaagcatcc tgt                                                            13

<210> SEQ ID NO 65
<211> LENGTH: 12
<212> TYPE: DNA
<213> ORGANISM: Artificial
<220> FEATURE:
<223> OTHER INFORMATION: LNA olgiomer
<220> FEATURE:
<221> NAME/KEY: misc_feature
<222> LOCATION: (1)..(12)
<223> OTHER INFORMATION: Phosphorothioate linkage
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (11)..(12)
<223> OTHER INFORMATION: LNA

<400> SEQUENCE: 65
gcaagcatcc tg                                                             12

<210> SEQ ID NO 66
<211> LENGTH: 3958
<212> TYPE: DNA
<213> ORGANISM: Homo sapiens

<400> SEQUENCE: 66
gtgctgcctc gtctgagggg acaggaggat caccctcttc gtcgcttcgg ccagtgtgtc         60
gggctgggcc ctgacaagcc acctgaggag aggctcggag ccgggcccgg accccggcga        120 tgccgcccg  cttctctcta gtctcacgag gggtttcccg cctcgcaccc ccacctctgg        180
acttgccttt cctctctcttc tccgcgtgtg gagggagcca gcgcttaggc cggagcgagc        240
ctgggggccg cccgccgtga agacatcgcg gggaccgatt caccatggag ggcgccggcg        300
gcgcgaacga caagaaaaag ataagttctg aacgtcgaaa agaaaagtct cgagatgcag        360
ccagatctcg gcgaagtaaa gaatctgaag ttttttatga gcttgctcat cagttgccac        420
ttccacataa tgtgagttcg catcttgata aggcctctgt gatgaggctt accatcagct        480
atttgcgtgt gaggaaactt ctggatgctg gtgatttgga tattgaagat gacatgaaag        540
cacagatgaa ttgcttttat ttgaaagcct tggatggttt tgttatggtt ctcacagatg        600
atggtgacat gatttacatt tctgataatg tgaacaaata catgggatta actcagtttg        660
aactaactgg acacagtgtg tttgatttta ctcatccatg tgaccatgag gaaatgagag        720
aaatgcttac acacagaaat ggccttgtga aaaagggtaa agaacaaaac acacagcgaa        780
gcttttttct cagaatgaag tgtacccctaa ctagccgagg aagaactatg aacataaagt        840
ctgcaacatg gaaggtattg cactgcacag gccacattca cgtatatgat accaacagta        900
accaacctca gtgtgggtat aagaaaccac ctatgacctg cttggtgctg atttgtgaac        960
ccattcctca cccatcaaat attgaaattc ctttagatag caagactttc ctcagtcgac       1020
acagcctgga tatgaaattt tcttattgtg atgaaagaat taccgaattg atgggatatg       1080
agccagaaga actttaggc cgctcaattt atgaatatta tcatgctttg gactctgatc       1140
atctgaccaa aactcatcat gatatgttta ctaaaggaca agtcaccaca ggacagtaca       1200
```

```
ggatgcttgc caaaagaggt ggatatgtct gggttgaaac tcaagcaact gtcatatata    1260
acaccaagaa ttctcaacca cagtgcattg tatgtgtgaa ttacgttgtg agtggtatta    1320
ttcagcacga cttgattttc tcccttcaac aaacagaatg tgtccttaaa ccggttgaat    1380
cttcagatat gaaatgact cagctattca ccaaagttga atcagaagat acaagtagcc     1440
tctttgacaa acttaagaag gaacctgatg cttttaacttt gctggcccca gccgctggag   1500
acacaatcat atctttagat tttggcagca acgacacaga aactgatgac cagcaacttg    1560
aggaagtacc attatataat gatgtaatgc tcccctcacc caacgaaaaa ttacagaata    1620
taaatttggc aatgtctcca ttacccaccg ctgaaacgcc aaagccactt cgaagtagtg    1680
ctgaccctgc actcaatcaa gaagttgcat taaaattaga accaaatcca gagtcactgg    1740
aactttcttt taccatgccc cagattcagg atcagacacc tagtccttcc gatggaagca    1800
ctagacaaag ttcacctgag cctaatagtc ccagtgaata ttgttttat gtggatagtg      1860 atatggtcaa tgaattcaag ttggaattgg tagaaaaact ttttgctgaa gacacagaag    1920
caaagaaccc attttctact caggacacag atttagactt ggagatgtta gctccctata    1980
tcccaatgga tgatgacttc cagttacgtt ccttcgatca gttgtcacca ttagaaagca    2040
gttccgcaag ccctgaaagc gcaagtcctc aaagcacagt tacagtattc cagcagactc    2100
aaatacaaga acctactgct aatgccacca ctaccactgc caccactgat gaattaaaaa    2160
cagtgacaaa agaccgtatg gaagacatta aaatattgat tgcatctcca tctcctaccc   2220
acatacataa agaaactact agtgccacat catcaccata tagagatact caaagtcgga    2280
cagcctcacc aaacagagca ggaaaaggag tcatagaaca gacagaaaaa tctcatccaa    2340
gaagccctaa cgtgttatct gtcgctttga gtcaaagaac tacagttcct gaggaagaac    2400
taaatccaaa gatactagct ttgcagaatg ctcagagaaa gcgaaaaatg aacatgatg     2460 gttcactttt tcaagcagta ggaattggaa cattattaca gcagccagac gatcatgcag    2520
ctactacatc acttttcttgg aaacgtgtaa aaggatgcaa atctagtgaa cagaatggaa    2580
tggagcaaaa gacaattatt ttaatacccct ctgatttagc atgtagactg ctggggcaat    2640
caatggatga aagtggatta ccacagctga ccagttatga ttgtgaagtt aatgctccta    2700
tacaaggcag cagaaaccta ctgcagggtg aagaattact cagagctttg gatcaagtta    2760
actgagcttt ttcttaattt cattccttt tttggacact ggtggctcac tacctaaagc      2820
agtctattta tattttctac atctaatttt agaagcctgg ctacaatact gcacaaactt    2880
ggttagttca attttttgatc cccttttctac ttaatttaca ttaatgctct tttttagtat     2940
gttctttaat gctggatcac agacagctca ttttctcagt tttttggtat ttaaaccatt     3000
gcattgcagt agcatcattt taaaaaatgc accttttat ttatttattt ttggctaggg      3060
agtttatccc ttttttcgaat tatttttaag aagatgccaa tataatttt gtaagaaggc      3120 agtaaccttt catcatgatc ataggcagtt gaaaaatttt tacaccttt ttttcacatt      3180 ttacataaat aataatgctt tgccagcagt acgtggtagc cacaattgca caatatattt    3240
tcttaaaaaa taccagcagt tactcatgga atatattctg cgtttataaa actagttttt    3300
aagaagaaat ttttttttggc ctatgaaatt gttaaacctg gaacatgaca ttgttaatca    3360
tataataatg attcttaaat gctgtatggt ttattattta aatgggtaaa gccatttaca     3420
taatatagaa agatatgcat atatctagaa ggtatgtggc atttatttgg ataaaattct    3480
caattcagag aaatcatctg atgtttctat agtcactttg ccagctcaaa agaaaacaat    3540
accctatgta gttgtggaag tttatgctaa tattgtgtaa ctgatattaa acctaaatgt    3600
```

-continued

```
tctgcctacc ctgttggtat aaagatattt tgagcagact gtaaacaaga aaaaaaaat     3660 catgcattct tagcaaaatt gcctagtatg ttaatttgct caaaatacaa tgtttgattt     3720
tatgcacttt gtcgctatta acatccttt tttcatgtag atttcaataa ttgagtaatt     3780
ttagaagcat tattttagga atatatagtt gtcacagtaa atatcttgtt ttttctatgt     3840
acattgtaca aatttttcat tccttttgct ctttgtggtt ggatctaaca ctaactgtat     3900
tgttttgtta catcaaataa acatcttctg tggaccagga aaaaaaaaaa aaaaaaa       3958
```

<210> SEQ ID NO 67
<211> LENGTH: 16
<212> TYPE: DNA
<213> ORGANISM: Artificial
<220> FEATURE:
<223> OTHER INFORMATION: anti-Hif1alpha oligomer sequence motif

<400> SEQUENCE: 67
tggcaagcat cctgta                                                    16

<210> SEQ ID NO 68
<211> LENGTH: 16
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (13)..(15)
<223> OTHER INFORMATION: LNA

<400> SEQUENCE: 68
tggcaagcat cctgta                                                    16

<210> SEQ ID NO 69
<211> LENGTH: 16
<212> TYPE: DNA
<213> ORGANISM: Artificial
<220> FEATURE:
<223> OTHER INFORMATION: Anti-Hif1alpha LNA oligomer
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (13)..(16)
<223> OTHER INFORMATION: Phosphorothioate linkages
<220> FEATURE:
<221> NAME/KEY: misc_feature
<222> LOCATION: (13)..(15)
<223> OTHER INFORMATION: LNA

<400> SEQUENCE: 69
tggcaagcat cctgta                                                    16

```
<210> SEQ ID NO 70
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: beta-D-oxy-LNA nucleotide analogue
<220> FEATURE:
<221> NAME/KEY: misc_feature
<222> LOCATION: (1)..(2)
<223> OTHER INFORMATION: x= phosphorothioate link or phosphorodiester
      link
<220> FEATURE:
<221> NAME/KEY: misc_feature
<222> LOCATION: (2)..(3)
<223> OTHER INFORMATION: x= phosphorothioate link or phosphorodiester
      link
<220> FEATURE:
<221> NAME/KEY: misc_feature
<222> LOCATION: (2)..(2)
<223> OTHER INFORMATION: beta-D-oxy-LNA nucleotide analogue
<220> FEATURE:
<221> NAME/KEY: misc_feature
<222> LOCATION: (3)..(4)
<223> OTHER INFORMATION: s= phosphorothioate link
<220> FEATURE:
<221> NAME/KEY: misc_feature
<222> LOCATION: (4)..(5)
<223> OTHER INFORMATION: s= phosphorothioate link
<220> FEATURE:
<221> NAME/KEY: misc_feature
<222> LOCATION: (5)..(6)
<223> OTHER INFORMATION: s= phosphorothioate link
<220> FEATURE:
<221> NAME/KEY: misc_feature
<222> LOCATION: (6)..(7)
<223> OTHER INFORMATION: s= phosphorothioate link
<220> FEATURE:
<221> NAME/KEY: misc_feature
<222> LOCATION: (7)..(8)
<223> OTHER INFORMATION: s= phosphorothioate link
<220> FEATURE:
<221> NAME/KEY: misc_feature
<222> LOCATION: (8)..(9)
<223> OTHER INFORMATION: s= phosphorothioate link
<220> FEATURE:
<221> NAME/KEY: misc_feature
<222> LOCATION: (9)..(10)
<223> OTHER INFORMATION: s= phosphorothioate link
<220> FEATURE:
<221> NAME/KEY: misc_feature
<222> LOCATION: (10)..(11)
<223> OTHER INFORMATION: s= phosphorothioate link
<220> FEATURE:
<221> NAME/KEY: misc_feature
<222> LOCATION: (11)..(12)
<223> OTHER INFORMATION: s= phosphorothioate link
<220> FEATURE:
<221> NAME/KEY: misc_feature
<222> LOCATION: (12)..(13)
<223> OTHER INFORMATION: x= phosphorothioate link or phosphorodiester
      link
<220> FEATURE:
<221> NAME/KEY: misc_feature
<222> LOCATION: (12)..(12)
<223> OTHER INFORMATION: beta-D-oxy-LNA nucleotide analogue
<220> FEATURE:
<221> NAME/KEY: misc_feature
<222> LOCATION: (13)..(14)
<223> OTHER INFORMATION: x= phosphorothioate link or phosphorodiester
      link
<220> FEATURE:
<221> NAME/KEY: misc_feature
<222> LOCATION: (13)..(13)
<223> OTHER INFORMATION: beta-D-oxy-LNA nucleotide analogue
```

```
<220> FEATURE:
<221> NAME/KEY: misc_feature
<222> LOCATION: (14)..(14)
<223> OTHER INFORMATION: beta-D-oxy-LNA nucleotide analogue, or a
      2-deoxynucleotide

<400> SEQUENCE: 70
ggcaagcatc ctgt                                                        14

<210> SEQ ID NO 71
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: beta-D-oxy-LNA nucleotide analogue
<220> FEATURE:
<221> NAME/KEY: misc_feature
<222> LOCATION: (1)..(2)
<223> OTHER INFORMATION: phosphorothioate link or phosphorodiester link
<220> FEATURE:
<221> NAME/KEY: misc_feature
<222> LOCATION: (2)..(2)
<223> OTHER INFORMATION: beta-D-oxy-LNA nucleotide analogue
<220> FEATURE:
<221> NAME/KEY: misc_feature
<222> LOCATION: (2)..(3)
<223> OTHER INFORMATION: phosphorothioate link or phosphorodiester link
<220> FEATURE:
<221> NAME/KEY: misc_feature
<222> LOCATION: (3)..(4)
<223> OTHER INFORMATION: phosphorothioate link
<220> FEATURE:
<221> NAME/KEY: misc_feature
<222> LOCATION: (4)..(5)
<223> OTHER INFORMATION: phosphorothioate link
<220> FEATURE:
<221> NAME/KEY: misc_feature
<222> LOCATION: (5)..(6)
<223> OTHER INFORMATION: phosphorothioate link
<220> FEATURE:
<221> NAME/KEY: misc_feature
<222> LOCATION: (6)..(7)
<223> OTHER INFORMATION: phosphorothioate link
<220> FEATURE:
<221> NAME/KEY: misc_feature
<222> LOCATION: (7)..(8)
<223> OTHER INFORMATION: phosphorothioate link
<220> FEATURE:
<221> NAME/KEY: misc_feature
<222> LOCATION: (8)..(9)
<223> OTHER INFORMATION: phosphorothioate link
<220> FEATURE:
<221> NAME/KEY: misc_feature
<222> LOCATION: (9)..(10)
<223> OTHER INFORMATION: phosphorothioate link
<220> FEATURE:
<221> NAME/KEY: misc_feature
<222> LOCATION: (10)..(11)
<223> OTHER INFORMATION: phosphorothioate link
<220> FEATURE:
<221> NAME/KEY: misc_feature
<222> LOCATION: (11)..(12)
<223> OTHER INFORMATION: phosphorothioate link
<220> FEATURE:
<221> NAME/KEY: misc_feature
<222> LOCATION: (12)..(12)
<223> OTHER INFORMATION: beta-D-oxy-LNA nucleotide analogue
<220> FEATURE:
<221> NAME/KEY: misc_feature
<222> LOCATION: (12)..(13)
<223> OTHER INFORMATION: phosphorothioate link or phosphorodiester link
<220> FEATURE:
<221> NAME/KEY: misc_feature
<222> LOCATION: (13)..(13)
```

-continued

```
<223> OTHER INFORMATION: beta-D-oxy-LNA nucleotide analogue
<220> FEATURE:
<221> NAME/KEY: misc_feature
<222> LOCATION: (13)..(14)
<223> OTHER INFORMATION: phosphorothioate link or phosphorodiester link
<220> FEATURE:
<221> NAME/KEY: misc_feature
<222> LOCATION: (14)..(14)
<223> OTHER INFORMATION: beta-D-oxy-LNA nucleotide analogue, or a
      2-deoxynucleotide

<400> SEQUENCE: 71
ttactgcctt ctta                                                       14

<210> SEQ ID NO 72
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: beta-D-oxy-LNA nucleotide analogue
<220> FEATURE:
<221> NAME/KEY: misc_feature
<222> LOCATION: (1)..(2)
<223> OTHER INFORMATION: phosphorothioate link
<220> FEATURE:
<221> NAME/KEY: misc_feature
<222> LOCATION: (2)..(2)
<223> OTHER INFORMATION: beta-D-oxy-LNA nucleotide analogue
<220> FEATURE:
<221> NAME/KEY: misc_feature
<222> LOCATION: (2)..(3)
<223> OTHER INFORMATION: phosphorothioate link
<220> FEATURE:
<221> NAME/KEY: misc_feature
<222> LOCATION: (3)..(4)
<223> OTHER INFORMATION: phosphorothioate link
<220> FEATURE:
<221> NAME/KEY: misc_feature
<222> LOCATION: (4)..(5)
<223> OTHER INFORMATION: phosphorothioate link
<220> FEATURE:
<221> NAME/KEY: misc_feature
<222> LOCATION: (5)..(6)
<223> OTHER INFORMATION: phosphorothioate link
<220> FEATURE:
<221> NAME/KEY: misc_feature
<222> LOCATION: (6)..(7)
<223> OTHER INFORMATION: phosphorothioate link
<220> FEATURE:
<221> NAME/KEY: misc_feature
<222> LOCATION: (7)..(8)
<223> OTHER INFORMATION: phosphorothioate link
<220> FEATURE:
<221> NAME/KEY: misc_feature
<222> LOCATION: (8)..(9)
<223> OTHER INFORMATION: phosphorothioate link
<220> FEATURE:
<221> NAME/KEY: misc_feature
<222> LOCATION: (9)..(10)
<223> OTHER INFORMATION: phosphorothioate link
<220> FEATURE:
<221> NAME/KEY: misc_feature
<222> LOCATION: (10)..(11)
<223> OTHER INFORMATION: phosphorothioate link
<220> FEATURE:
<221> NAME/KEY: misc_feature
<222> LOCATION: (11)..(12)
<223> OTHER INFORMATION: phosphorothioate link
<220> FEATURE:
<221> NAME/KEY: misc_feature
<222> LOCATION: (12)..(12)
<223> OTHER INFORMATION: beta-D-oxy-LNA nucleotide analogue
<220> FEATURE:
<221> NAME/KEY: misc_feature
```

```
<222> LOCATION: (12)..(13)
<223> OTHER INFORMATION: phosphorothioate link
<220> FEATURE:
<221> NAME/KEY: misc_feature
<222> LOCATION: (13)..(13)
<223> OTHER INFORMATION: beta-D-oxy-LNA nucleotide analogue
<220> FEATURE:
<221> NAME/KEY: misc_feature
<222> LOCATION: (13)..(14)
<223> OTHER INFORMATION: phosphorothioate link

<400> SEQUENCE: 72
ggcaagcatc ctgt                                                       14

<210> SEQ ID NO 73
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (1)..(1)
<223> OTHER INFORMATION: beta-D-oxy-LNA nucleotide analogue
<220> FEATURE:
<221> NAME/KEY: misc_feature
<222> LOCATION: (1)..(2)
<223> OTHER INFORMATION: phosphorothioate link
<220> FEATURE:
<221> NAME/KEY: misc_feature
<222> LOCATION: (2)..(3)
<223> OTHER INFORMATION: phosphorothioate link
<220> FEATURE:
<221> NAME/KEY: misc_feature
<222> LOCATION: (2)..(2)
<223> OTHER INFORMATION: beta-D-oxy-LNA nucleotide analogue
<220> FEATURE:
<221> NAME/KEY: misc_feature
<222> LOCATION: (3)..(4)
<223> OTHER INFORMATION: phosphorothioate link
<220> FEATURE:
<221> NAME/KEY: misc_feature
<222> LOCATION: (4)..(5)
<223> OTHER INFORMATION: phosphorothioate link
<220> FEATURE:
<221> NAME/KEY: misc_feature
<222> LOCATION: (5)..(6)
<223> OTHER INFORMATION: phosphorothioate link
<220> FEATURE:
<221> NAME/KEY: misc_feature
<222> LOCATION: (6)..(7)
<223> OTHER INFORMATION: phosphorothioate link
<220> FEATURE:
<221> NAME/KEY: misc_feature
<222> LOCATION: (7)..(8)
<223> OTHER INFORMATION: phosphorothioate link
<220> FEATURE:
<221> NAME/KEY: misc_feature
<222> LOCATION: (8)..(9)
<223> OTHER INFORMATION: phosphorothioate link
<220> FEATURE:
<221> NAME/KEY: misc_feature
<222> LOCATION: (9)..(10)
<223> OTHER INFORMATION: phosphorothioate link
<220> FEATURE:
<221> NAME/KEY: misc_feature
<222> LOCATION: (10)..(11)
<223> OTHER INFORMATION: phosphorothioate link
<220> FEATURE:
<221> NAME/KEY: misc_feature
<222> LOCATION: (11)..(12)
<223> OTHER INFORMATION: phosphorothioate link
<220> FEATURE:
<221> NAME/KEY: misc_feature
<222> LOCATION: (12)..(13)
<223> OTHER INFORMATION: phosphorothioate link
<220> FEATURE:
<221> NAME/KEY: misc_feature
```

```
<222> LOCATION: (12)..(12)
<223> OTHER INFORMATION: beta-D-oxy-LNA nucleotide analogue
<220> FEATURE:
<221> NAME/KEY: misc_feature
<222> LOCATION: (13)..(14)
<223> OTHER INFORMATION: phosphorothioate link
<220> FEATURE:
<221> NAME/KEY: misc_feature
<222> LOCATION: (13)..(13)
<223> OTHER INFORMATION: beta-D-oxy-LNA nucleotide analogue

<400> SEQUENCE: 73
ttactgcctt ctta                                                            14

<210> SEQ ID NO 74
<211> LENGTH: 14
<212> TYPE: DNA
<213> ORGANISM: Artificial
<220> FEATURE:
<223> OTHER INFORMATION: LNA oligomer
<220> FEATURE:
<221> NAME/KEY: misc_feature
<222> LOCATION: (14)..(14)
<223> OTHER INFORMATION: beta-D-oxy-LNA nucleotide analogue, or a
      2-deoxynucleotide

<400> SEQUENCE: 74
ttactgcctt ctta                                                            14
```

SHORT OLIGOMER ANTAGONIST COMPOUNDS FOR THE MODULATION OF TARGET MRNA

CROSS-REFERENCE TO RELATED APPLICATIONS

The present application is a U.S. National Phase of International Application No. PCT/EP2008/053314, filed Mar. 19, 2008, which claims the benefit of U.S. Provisional Application No. 60/896,419, filed Mar. 22, 2007; U.S. Provisional Application No. 60/969,016, filed Aug. 30, 2007; U.S. Provisional Application No. 60/972,932, filed Sep. 17, 2007; U.S. Provisional Application No. 60/977,409, filed Oct. 4, 2007; International Application No. PCT/EP2007/060703, filed Oct. 9, 2007; U.S. Provisional Application No. 60/990,125, filed Nov. 26, 2007; U.S. Provisional Application No. 60/992,050, filed Dec. 3, 2007; U.S. Provisional Application No. 61/012,191, filed Dec. 7, 2007; U.S. Provisional Application No. 61/012,185, filed Dec. 7, 2007; U.S. Provisional Application No. 61/023,244, filed Jan. 24, 2008; and 61/023,250, filed Jan. 24, 2008; each of which is incorporated herein by reference.

REFERENCE TO SEQUENCE LISTING SUBMITTED ELECTRONICALLY

The content of the electronically submitted sequence listing (Name Sequence-_Listing__2.txt; Size: 30,961 bytes; and Date of Creation: Mar. 16, 2010) filed with the application is incorporated herein by reference in its entirety.

FIELD OF THE INVENTION

The present invention provides antisense oligonucleotides (oligomers), compositions and methods for modulating the expression of target mRNAs. In a particularly interesting aspect, the invention provides LNA gapmer oligomers, which have a total of between 1 and three, such as one or two phosphodiester internucleoside linkages. Such oligomers have been found to have superior bioavailability and have also been found to selectively accumulate in kidney cells.

RELATED CASES

The following applications are hereby incorporated by reference: U.S. 60/896,419, U.S. 60/969,016, 60/969,419, U.S. 60/828,735, U.S. 60/972,932, U.S. 61/012,185, U.S. 61/012,191, U.S. 60/992,050, and U.S. 60/990,125.

BACKGROUND

Zhou and Agrawal et al, Bioorganic & Medicinal Chemistry Letters 8 (1998) 3269-3274, reports on 2'-O methylribonucleoside gapmer phosphorothioate oligonucleotides, which have flanks which each comprise four and five 2'-O methylribonucleoside units, where each flank comprises two phosphodiester bonds. The introduction of phosphodiester bonds was found to result in intravenous distribution patterns similar to the fully phosphorothioate molecules, but have reduced side effects.

SUMMARY OF THE INVENTION

The invention provides for an oligomer consisting of a contiguous nucleobase sequence of a total of between 10-20 nucleobases, such as 11, 12, 13, 14, 15, 16, 17, 18, 19 nucleobase units, wherein the contiguous nucleobase sequence is of formula (5'-3'), A-B-C, or optionally A-B-C-D or D-A-B-C, wherein;
  region A (5' region) consists or comprises of at least one nucleotide analogue, such as at least one LNA unit, such as between 1-6 nucleotide analogues, such as LNA units, preferably between 2-5 nucleotide analogues, such as 2-5 LNA units, such as 3 or 4 nucleotide analogues, such as 3 or 4 LNA units and;
  region B (central domain), preferably immediately 3' (i.e. contiguous) to A, consists of between 6-12 contiguous nucleobase units which are capable of recruiting RNAseH when formed in a duplex with a complementary RNA molecule (such as a mRNA target) such as DNA units; preferably region B comprises of at least one DNA sugar unit, such as 1-12 DNA units, preferably between 4-12 DNA units, more preferably region B consists of between 6-10 DNA units, such as between 7-10 DNA units, most preferably 8, 9 or 10 DNA units, and;
  region C(3' region) preferably immediately 3' to B, consists or comprises at of at least one nucleotide analogues, such as at least one LNA unit, such as between 1-6 nucleotide analogues, such between 2-5 nucleotide analogues, such as between 2-5 LNA units, such as 3 or 4 nucleotide analogues, such as 3 or 4 LNA units; and
  region D, when present, consists of one or two DNA units
  wherein said oligomer comprises of a total of 1, 2 or 3 phosphodiester linkages; preferably the phosphodiester bond or bonds are inserted between or adjacent to nucleotide analogue(s) of region A and/or C.

The invention provides for an oligomer consisting of a contiguous nucleobase sequence of a total of 10, 11, 12, 13, 14, 15 or 16 nucleobase units, wherein the contiguous nucleobase sequence is of formula (5'-3'), A-B-C, or optionally A-B-C-D or D-C-B-A, wherein:
  A consists of 1, 2 or 3 LNA units;
  B consists of 7, 8, or 9 contiguous nucleobase units which are capable of recruiting RNAseH when formed in a duplex with a complementary RNA molecule (such as a mRNA target); and
  C consists of 1, 2 or 3 LNA units; and
  D, where present, consists of 1 DNA unit.

In one embodiment, the oligomer comprises a total of one, two or three phosphodiester bonds. In such an embodiment, preferably the remaining internucleoside linkages are phosphorothioate linkages.

The invention provides for an oligomer consisting of a contiguous nucleobase sequence of a total of 10, 11, 12, 13 or 14 nucleobase units, wherein the contiguous nucleobase sequence is of formula (5'-3'), A-B-C, or optionally A-B-C-D or D-C-B-A, wherein; region A consists of 1, 2 or 3 LNA units; region B consists of 7, 8 or 9 contiguous nucleobase units which are capable of recruiting RNAseH when formed in a duplex with a complementary RNA molecule (such as a mRNA target); and region C consists of 1, 2 or 3 LNA units; and wherein said oligomer comprises of a total of 1 or 2 phosphodiester linkages; and region D, when present, consists of one DNA unit.

The invention further provides a conjugate comprising the oligomer according to the invention, such as a conjugate which, in addition to the nucleobase sequence of the oligomer comprises at least one non-nucleotide or non-polynucleotide moiety covalently attached to the oligomer of the invention.

The invention provides for pharmaceutical composition comprising the oligomer or conjugate of the invention, and a pharmaceutically acceptable diluent, carrier, salt or adjuvant.

The invention further provides for an oligomer according to the invention, for use in medicine.

The invention further provides for the use of the oligomer of the invention for the manufacture of a medicament for the treatment of one or more of the diseases referred to herein.

The invention further provides for an oligomer according to the invention, for use for the treatment of one or more of the diseases referred to herein.

The invention provides for a method for the treatment of one or more of the diseases referred to herein in a patient suffering from said disease, said method comprising administering the oligomer, conjugate or pharmaceutical of the invention to said patient.

The invention provides for a method of inhibiting or reducing the level of a target mRNA in a cell or a tissue, the method comprising the step of contacting said cell or tissue with on oligomer, a conjugate, or a pharmaceutical composition according to the invention so that level of target mRNA is inhibited or reduced.

The invention provides for a method of inhibiting or reducing the level of a target protein in a cell or a tissue, the method comprising the step of contacting said cell or tissue with on oligomer, a conjugate, or a pharmaceutical composition according to the invention so that level of target protein is inhibited or reduced. In one embodiment the target protein is Hif1alpha.

The invention provides for a method for the reduction in the cellular concentration of a mRNA in a mammalian cell, said method comprising the administration of an oligomer, or the conjugate according to the invention, to the mammalian cell, wherein said mammalian cell comprises an mRNA species which comprises a nucleobase sequence which is complementary to said oligomer.

The invention provides for a method for modifying a fully phosphorothioate oligomer to enhance its accumulation or bioavailability in an organ, said method comprising replacing a total of one or two of the phosphorothioate linkages with phosphodiester bonds, wherein said oligomers consist of a contiguous nucleobase sequence A-B-C, or A-B-C-D, or D-A-B-C, as defined in one of the embodiments herein.

The invention provides for a method for modifying a fully phosphorothioate oligomer to enhance its accumulation or bioavailability in an organ, said method comprising replacing a total of one, two or three, such as one or two of the phosphorothioate linkages with phosphodiester bonds, wherein said oligomers consisting of a contiguous nucleobase sequence of a total of 10-25 nucleobase units, such as 11, 12, 13, 14, 15, 16, 17, 18, 19, 20, 21, 22, 23, or 25 nucleobase units wherein the contiguous nucleobase sequence is of formula (5'-3'), A-B-C, A-B-C-D or D-A-B-C; wherein region A (5' region) consists or comprises of at least one nucleotide analogue, such as at least one LNA unit, such as between 1-6 nucleotide analogues, such as 2, 3, 4 or 5 nucleotide analogue units, such as LNA units, preferably between 2-5 nucleotide analogues, such as 2-5 LNA units, such as 3 or 4 nucleotide analogues, such as 3 or 4 LNA units and; region B (central domain), preferably immediately 3' (i.e. contiguous) to A, consists or comprises at least one DNA sugar unit, such as 1-12 DNA units, preferably between 4-12 DNA units, more preferably between 6-10 DNA units, such as between 7-10 DNA units, most preferably 8, 9 or 10 DNA units, and; region C (3' region) preferably immediately 3' to B, consists or comprises at of at least one nucleotide analogues, such as at least one LNA unit, such as between 1-6 nucleotide analogues, such as 2, 3, 4 or 5 nucleotide analogue units, such between 2-5 nucleotide analogues, such as between 2-5 LNA units, most preferably 3 or 4 nucleotide analogues, such as 3 or 4 LNA units, and, when present region D consists of 1, 2 or 3 nucleotide units, such as DNA. Preferably the phosphodiester bonds are inserted between or adjacent to nucleotide analogue(s) of region A and/or C. In one embodiment region B consists of 11 nucleobases, such as DNA units.

In one embodiment, the oligomer targets Hif-1alpha mRNA (e.g. SEQ ID NO 66).

In one embodiment, the oligomeric compound consists of a total of 10-15 or 10-16 nucleobases, wherein the nucleobase sequence of said compound corresponds to a contiguous subsequence present in the hifl-alpha mRNA (e.g. SEQ ID NO 66), wherein said compound comprises at least 2 or at least 3 nucleotide analogues.

In one embodiment, the oligomer consists of a total of 10-15, or 10-16 nucleobases, wherein the nucleobase sequence of said compound corresponds to a contiguous subsequence present in SEQ ID NO 51, 52, 53, 54 or 55, wherein said compound comprises at least 2 or at least 3 nucleotide analogues.

The invention provides for a method of down-regulating hif-1alpha in a cell, said method comprising administering the oligomer or conjugate according to the invention to a cell which is expressing Hif1-alpha so that the expression of hif-1alpha in the cell is reduced.

The invention further provides for the use of the oligomer targeting Hif-1alpha, or a conjugate thereof, for the manufacture of a medicament for the treatment of cancer.

The invention further provides for the oligomer targeting Hif-1alpha, or a conjugate thereof, as a medicament, such as a medicament for the treatment of cancer.

The invention further provides for a method for treating cancer, said method comprising administering the use of the oligomer targeting Hif-1alpha, or a conjugate or a pharmaceutical composition which comprises said oligomer to a patient in need thereof (typically one suffering from cancer).

DETAILED DESCRIPTION OF THE INVENTION

Figure 1:
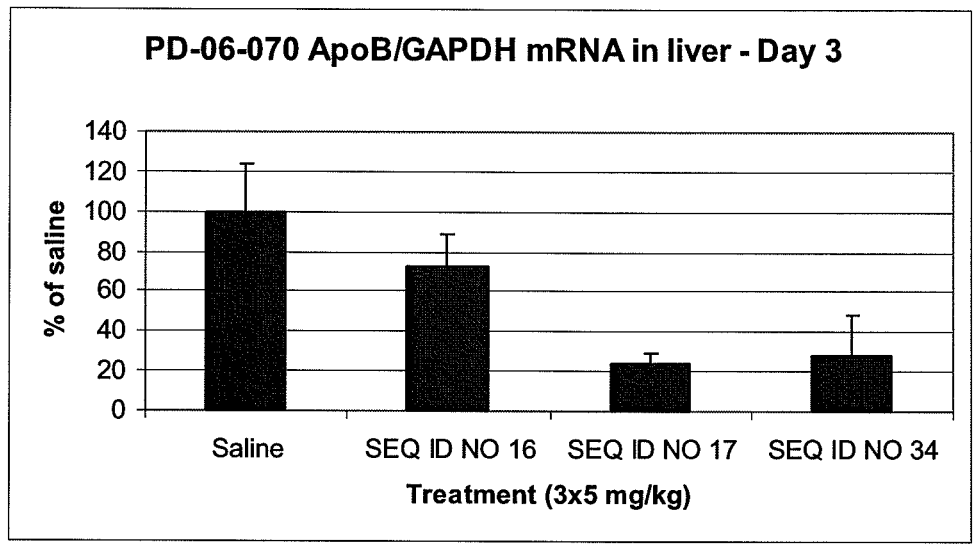
FIG. 1. The apoB-100 mRNA expression was measured by qPCR normalized to the house keeping gene GAPDH and presented relative to the saline group. Mice (n=3 or 5) were dosed 3 consecutive days and sacrifice 24 hours after the last dosing, liver was isolated and analyzed.

U.S. provisional application 60/977,409 is hereby incorporated by reference. The present invention provides oligomeric compounds (oligomers), compositions, and methods, for modulating the expression of target mRNAs. In a particularly interesting aspect, the invention provides LNA gapmer oligomers of between 10-20, 10-16, or 10-14 nucleobases in length, which have a total of between 1-3, such as 1 or 2 phosphodiester internucleoside linkages. Such oligomers have been found to have superior bioavailability and have also been found to selectively accumulate in kidney cells.

Oligomers with the A-B-C or A-B-C-D or D-A-B-C design are referred to as gapmers herein. Gapmers of between 10-14 nucleobases are also referred to as shortmers. Suitably, the length of the oligomer (contiguous nucleobase sequence) may be 10, 11, 12, 13, 14, 15, 16, 17, 18, 19, or 20 nucleobases in length. An a preferred embodiment, oligomer of the invention consists or comprises of a contiguous nucleobase sequence of (a total of) between 10 and 16, such as 15 or 16 nucleobases, or 10 and 14 nucleobases, such as 11, 12, and 13 nucleobases, and preferably between 10 and 13 nucleobases.

In one embodiment, the oligomer of the invention consists of a nucleobase sequence with is 100% complementary to a corresponding region of the target mRNA.

In one embodiment, the terms "oligomeric compound" or "oligomer", which are used interchangeably, refer to an oligonucleotide (which may comprise nucleotides and nucleotide analogues) which can induce a desired therapeutic effect in humans through for example binding by hydrogen bonding to a target nucleic acid. It is also envisaged that the oligomeric compounds disclosed herein may have non-therapeutic applications, such as diagnostic applications. Then oligomer is a single stranded (antisense) oligonucleotide.

In one embodiment, the oligomer of the invention does not comprise RNA units.

The oligomeric compounds may hybridize to any site along the target mRNA nucleic acid, such as the 5' untranslated leader, exons, introns and 3' untranslated tail. However, it is preferred that the oligonucleotides hybridise to the mature mRNA form of the target nucleic acid.

When designed as an antisense inhibitor, for example, the oligonucleotides of the invention bind to the target nucleic acid and modulate the expression of its cognate protein. Preferably, such modulation produces an inhibition of expression of at least 10% or 20% compared to the normal expression level, more preferably at least a 30%, 40%, 50%, 60%, 70%, 80%, 90% or 95% inhibition compared to the normal expression level. Suitably, such modulation is seen when using between 5 and 25 nM concentrations of the compound of the invention. In the same of a different embodiment, the inhibition of expression is less than 100%, such as less than 98% inhibition, less than 95% inhibition, less than 90% inhibition, less than 80% inhibition, such as less than 70% inhibition. Modulation of expression level is determined by measuring protein levels, e.g. by the methods such as SDS-PAGE followed by western blotting using suitable antibodies raised against the target protein. Alternatively, modulation of expression levels can be determined by measuring levels of mRNA, eg. by northern blotting or quantitative RT-PCR. When measuring via mRNA levels, the level of down-regulation when using an appropriate dosage, such as between 5 and 25 nM concentrations, is, in one embodiment, typically to a level of between 10-20% the normal levels in the absence of the compound of the invention.

The terms "corresponding to" and "corresponds to" refer to the comparison between the nucleobase sequence of the oligomer (the contiguous nucleobase sequence) and the equivalent nucleotide sequence of i) the reverse complement of the nucleic acid target, such as the mRNA which encodes the target protein (e.g. Hif-1alpha), and/or ii) the sequence of nucleotides provided herein such as the group consisting of SEQ ID NOS: 51-55. Nucleotide analogues are compared directly to their equivalent or corresponding nucleotides. Therefore, in one embodiment, the terms "corresponding to"/ "corresponds to" refer to the comparison between the combined sequence of nucleotides and nucleotide analogues of the oligomeric compound of the invention, or subsequence thereof, and the equivalent nucleotide sequence of Apolipoprotein B or Hif1alpha nucleic acid sequence (i.e. the nucleic acid target).

Nucleotide analogues are compared directly to their equivalent or corresponding nucleotides.

The terms "corresponding nucleotide analogue" and "corresponding nucleotide" are intended to indicate that the nucleobase in the nucleotide analogue and the nucleotide are identical. For example, when the 2-deoxyribose unit of the nucleotide is linked to an adenine, the "corresponding nucleotide analogue" contains a pentose unit (different from 2-deoxyribose) linked to an adenine.

The term "nucleobase" is used as a collective term which encompasses both nucleotides and nucleotide analogues. A nucleobase sequence is a sequence which comprises at least two nucleotides or nucleotide analogues. In one embodiment the nucleobase sequence may comprise of only nucleotides, such as DNA units, in an alternative embodiment, the nucleobase sequence may comprise of only nucleotide analogues, such as LNA units.

The term "nucleic acid" is defined as a molecule formed by covalent linkage of two or more nucleotides.

The terms "nucleic acid" and "polynucleotide" are used interchangeable herein.

The term "target nucleic acid", as used herein refers to the DNA or RNA sequence encoding the mammalian target polypeptide (target for down-regulation). In one embodiment, for example when used in research or diagnostics the "target nucleic acid" may be a cDNA or a synthetic oligonucleotide derived from the above DNA or RNA nucleic acid targets. The oligomer according to the invention is preferably capable of hybridising to the target nucleic acid.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth.

Target Sequences

The target of the oligomers of the invention is typically a mRNA which is comprises a nucleotide sequence which is complementary (or essentially complementary—e.g. may, in one embodiment comprise one or two mismatches) to the contiguous nucleobase sequence of the oligomer of the invention—i.e. the nucleotide region of the target 'corresponds' to the contiguous nucleobase sequence of the oligomer.

In one embodiment the target mRNA is a mammalian mRNA, such as a human mRNA, selected form the group consisting of ApoB-100 or Hif-1alpha, (see SEQ ID NO 66 for human hif 1 alpha sequence—Genbank accession number NM_001530), and naturally occurring allelic variants and homologues thereof.

In the tables of oligonucleotides herein, which include specific oligomers according to the invention—regions A and C are in bold, regions B and where present D, are not in bold. A superscript $^m$ prior to the base letter C, refers to methyl-cytosine; a subscript $_s$ after the base letter, refers to a phosphorothioate linkage; a superscript $^o$ after the base letter refers to oxy-LNA, particularly beta-D-oxy-LNA. It should be noted that that, in one embodiment, other LNA monomers as disclosed herein, may be used in place of oxy-LNA. It should be noted that that, in one embodiment, non-methylated LNA cytosine monomer may be used.

ApoB-100—see U.S. 60/896,419—hereby incorporated by reference—US60/896,419 provides the medical disorders associated with abnormal ApoB100 levels which may be treated with oligomers of the invention targeting ApoB100. See the examples for oligomers targeting ApoB.

Hif-1alpha—WO2006/050734—hereby incorporated by reference provides medical disorders associated with abnormal Hif-1alpha levels which may be treated with oligomers of the invention targeting Hif-1alpha. Specifically preferred oligomers targeting Hif-1alpha include:

| | | | |
|---|---|---|---|
| SEQ ID NO: 41 | 14 | 2-9-2 | 5'-GGcaagcatccTGt-3' |
| SEQ ID NO: 42 | 14 | 2-8-3 | 5'-GGcaagcatccCTGt-3' |
| SEQ ID NO: 43 | 14 | 3-7-3 | 5'-GGCaagcatcCTGt-3' |
| SEQ ID NO: 44 | 13 | 2-9-2 | 5'-GGcaagcatccTG-3' |
| SEQ ID NO: 45 | 13 | 2-8-3 | 5'-GGcaagcatgCTG-3' |
| SEQ ID NO: 46 | 13 | 2-8-3 | 5'-GCaagcatccTGT-3' |
| SEQ ID NO: 47 | 13 | 2-9-2 | 5'-GCaagcatcctGT-3' |
| SEQ ID NO: 48 | 12 | 1-9-2 | 5'-GcaagcatccTG-3' |
| SEQ ID NO: 49 | 12 | 2-8-2 | 5'-GCaagcatccTG-3' |
| SEQ ID NO: 50 | 12 | 2-7-3 | 5'-GCaagcatcCTG-3' |
| SEQ ID NO: 51 | | | 5'-GGCAAGCATCCTGT-3' |
| SEQ ID NO: 52 | | | 5'-GGCAAGCATCCTG-3' |
| SEQ ID NO: 53 | | | 5'-GCAAGCATCCTGT-3' |
| SEQ ID NO: 54 | | | 5'-GCAAGCATCCTG-3' |
| SEQ ID NO: 55 | | | TGGCAAGCATCCTGTA |

Hif-1a oligomer sequence motifs. In one embodiment the oligomeric compound of the invention has a sequence motif (contiguous nucleobase sequence) which is found within or is identical to any one of SEQ ID 41-55.

Specific HIF-1a Targeting Compounds

| Test substance | Sequence | Size |
|---|---|---|
| SEQ ID NO: 56 | 5'-$T_s^oG_s^oG_s^oc_sa_sa_sg_sc_sa_st_sc_sT_s^oG_s^oT_s^o$a-3' | 16 |
| SEQ ID NO: 57 | 5'-$G_s^oG_s^oc_sa_sa_sg_sc_sa_st_sc_sT_s^oG_s^o$t-3' | 14 |
| SEQ ID NO: 58 | 5'-$G_s^oC_s^oa_sa_sg_sc_sa_st_sc_sT_s^oG^o$-3' | 12 |
| SEQ ID NO: 59 | 5'-$G_s^oG_s^{o\,m}C_s^oa_sa_sg_sc_sa_st_sc_sT_s^oG_s^oT^o$-3' | 14 |
| SEQ ID NO: 60 | 5'-$G_s^oG_s^oc_sa_sa_sg_sc_sa_st_sc_sT_s^oG_s^oT^o$-3' | 14 |
| SEQ ID NO: 61 | 5'-$G_s^oG_s^oc_sa_sa_sg_sc_sa_st_sc_sT_s^oG^o$-3' | 13 |
| SEQ ID NO: 62 | 5'-$G_s^oG_s^oc_sa_sa_sg_sc_sa_st_sc_s^{m}C_s^oT_s^oG^o$-3' | 13 |
| SEQ ID NO: 63 | 5'-$G_s^{o\,m}C_s^oa_sa_sg_sc_sa_st_sc_sT_s^oG_s^oT^o$-3' | 13 |
| SEQ ID NO: 64 | 5'-$G_s^{o\,m}C_s^oa_sa_sg_sc_sa_st_sc_sc_st G_s^oT^o$-3' | 13 |
| SEQ ID NO: 65 | 5'-$G_s^oc_sa_sa_sg_sc_sa_st_sc_sT_s^oG^o$-3' | 12 |

In one embodiment, the oligomer of the invention is selected from SEQ ID NO 57, 58, 59, 60, 61, 62, 63, 64 and 65. In one embodiment, the oligomer of the invention is SEQ ID NO 68 or 69. In one embodiment, the oligomer of the invention is SEQ ID NO 56. In one embodiment the nucleobase sequence selected from the group consisting of SEQ ID NOS 51, 52, 53, 54, or 55 (motif sequences), or a corresponding subsequence thereof.

In one embodiment, the oligomeric compound of the invention consists of a contiguous nucleobase sequence of a total of 10-14 nucleobases in length.

A 'corresponding subsequence' in this context, refers to the situation where the oligomer of the invention is shorter than the respective sequence selected from the group consisting of SEQ ID NOS 51, 52, 53, 54 or 55, (or SEQ ID NO 66) but the contiguous sequence of bases present in the oligomer is found within the respective sequence.

In one embodiment, the contiguous nucleobase sequence consists of a total of 10, 11, 12, 13 or 14 nucleobase units, preferably 10, 11, 12 or 13, present in, or corresponding to (such as the same base (A, T, C or G) sequence) the nucleobase sequence of the oligomer sequences shown in any one of tables of sequences or compounds disclosed herein.

In one embodiment, the contiguous nucleobase sequence consists of a total of 15 or 16 nucleobase units, present in, or corresponding to (such as the same base (A, T, C or G) sequence) the nucleobase sequence of the oligomer sequences shown in any one of tables of sequences or compounds disclosed herein.

In one embodiment, the oligomer of the invention may comprise both a polynucleotide region, i.e. a nucleobase region, which typically consists of a contiguous sequence of nucleobases/nucleotides, and a further non-nucleobase region. When referring to the compound of the invention consisting of a nucleobase sequence, the compound may comprise non-nucleobase components, such as a conjugate component.

Alternatively, the oligomer of the invention may consist entirely of a nucleobase region.

In one embodiment, the oligomer according to the invention is not: 5'-$G_xG_xc_sa_sa_sg_sc_sa_st_sc_sc_sT_xG_x\underline{T}$-3' (SEQ ID NO:70) or 5'-$T_xT_xa_sc_st_sg_sc_sc_st_st_sc_sT_xT_xA$-3' (SEQ ID NO:71) or 5'-$G_sG_sc_sa_sa_sg_sc_sa_st_sc_sc_sT_sG_st$-3' (SEQ ID NO:72) or 5'-$T_sT_sa_sc_st_sg_sc_sc_st_st_sc_sT_sT_sa$-3' (SEQ ID NO:73) (as disclosed in WO2006/050734) wherein capital letters designate a beta-D-oxy-LNA nucleotide analogue, small letters designate a 2-deoxynucleotide, underline designates either a beta-D-oxy-LNA nucleotide analogue or a 2-deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

In one embodiment, the nucleobase sequence of the oligomer according to the invention is not: 5'-GGCAAGCATC-CTGT-3' (SEQ ID NO:41) or 5'-TTACTGCCTTCTT$\underline{A}$-3' (SEQ ID NO:74).

In one, not necessarily limiting embodiment, the nucleobase sequence of the oligomer according to the invention is not complementary to a Hif1-alpha target sequence.

In some embodiments of oligomer according to the invention, such as an antisense oligonucleotide which comprises LNA, all LNA C units are 5' methyl-Cytosine ($^mC$).

In most preferred embodiments the oligomer comprises only LNA nucleotide analogues and nucleotides (RNA or DNA, most preferably DNA nucleotides), optionally with modified internucleobase linkages such as phosphorothioate, or, as described herein predominantly (or fully) phosphorothioate linkages, but with the exception of 1-3, such as 1 or 2 phosphodiester linkages.

Locked Nucleic Acid (LNA)

The term "LNA" refers to a bicyclic nucleotide analogue, known as "Locked Nucleic Acid". It may refer to an LNA monomer, or, when used in the context of an "LNA oligonucleotide" refers to an oligonucleotide containing one or more such bicyclic nucleotide analogues.

The LNA used in the oligonucleotide compounds of the invention preferably has the structure of the general formula I

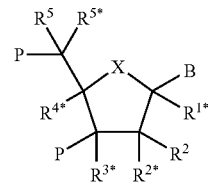

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, natural or non-natural nucleobases, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from O, S, and N($R^a$), and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di($C_{1-6}$-alkyl)amino, tris($C_{1-6}$-alkyl)ammonium, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$) or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and $C_{1-4}$-alkyl, and each of the substituents $R^{1*}$, $R^2$, $R^3$, $R^5$, $R^{5*}$, $R^6$ and $R^{6*}$, are independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof;

In one embodiment $R^{5*}$ is selected from H, —$CH_3$, —$CH_2$—$CH_3$, —$CH_2$—O—$CH_3$, and —CH=$CH_2$. In one embodiment, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—; wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents together may designate optionally substituted methylene (=$CH_2$) or together may form a spiro biradical consisting of a 1-5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl.

In a further embodiment $R^{4*}$ and $R^{2*}$ together designate a biradical selected from —$CH_2$—O—, —$CH_2$—S—, —$CH_2$—NH—, —$CH_2$—N($CH_3$)—, —$CH_2$—$CH_2$-O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, —CH($CH_2$—O—$CH_3$)—O—.

All chiral centers may be found in either R or S orientation.

Preferably, the LNA used in the oligomer of the invention comprises at least one LNA unit according to any of the formulas

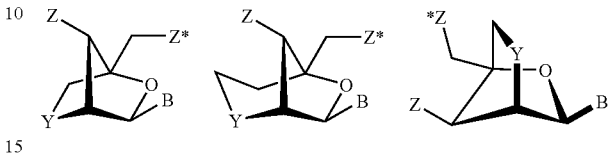

wherein Y is —O—, —S—, —NH—, or N($R^H$); Z and $Z^*$ are independently selected among an internucleoside linkage, a terminal group or a protecting group; B constitutes a natural or non-natural nucleotide base moiety, and $R^H$ is selected from hydrogen and $C_{1-4}$-alkyl.

The term "thio-LNA" comprises a locked nucleotide in which Y in the formulas above represents S. Thio-LNA can be in both beta-D and alpha-L-configuration.

The term "amino-LNA" comprises a locked nucleotide in which Y in the formulas above is selected from —N(H)—, and N($R^H$)—, where $R^H$ is selected from hydrogen and $C_{1-4}$-alkyl. Amino-LNA can be in both beta-D and alpha-L-configuration.

The term "oxy-LNA" comprises a locked nucleotide in which Y in the formulas above represents —O—. Oxy-LNA can be in both beta-D and alpha-L-configuration.

The term "ENA" comprises a locked nucleotide in which Y in the formulas above is —$CH_2$—O— (where the oxygen atom of —$CH_2$—O— is attached to the 2'-position relative to the base B). ENA can be in both beta-D and alpha-L-configuration. In a preferred embodiment LNA is selected from beta-D-oxy-LNA, alpha-L-oxy-LNA, beta-D-amino-LNA and beta-D-thio-LNA, in particular beta-D-oxy-LNA. Specifically preferred LNA units are shown in scheme 2:

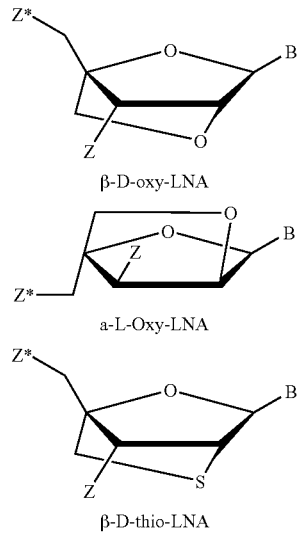

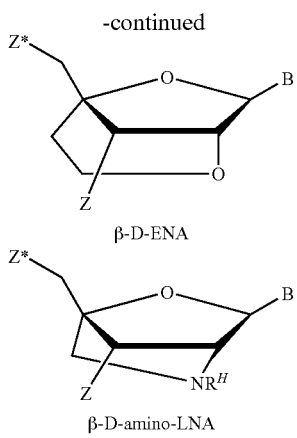

β-D-ENA

β-D-amino-LNA

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^N$—CO—O—, where R$^H$ is selected form hydrogen and C$_{1-4}$-alkyl.

When used herein, the term "DNA intercalator" means a group which can intercalate into a DNA or RNA helix, duplex or triplex. (Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin.)? Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphthoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that comprises more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, europium, ruthenium, samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. Cu$^{2+}$, Mg$^{2+}$) bound to a biological molecule being detectable by the use of electron spin resonance spectroscopy), enzymes (such as peroxidases, alkaline phosphatases, β-galactosidases, and glucose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesterol), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, ruthenium, europium, Cy5 and Cy3.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, C$_1$-C$_{20}$ alkyl groups optionally interrupted or terminated with one or more heteroatoms such as oxygen atoms, nitrogen atoms, and/or sulphur atoms, optionally comprising aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

The LNA used in the oligonucleotide compounds of the invention preferably has the structure of the general formula

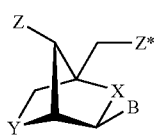

where X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably the LNA units comprise at least one beta-D-oxy-LNA unit(s) such as 2, 3, 4, 5 or 6 beta-D-oxy-LNA units.

In the present context, the term "C1-4-alkyl" is intended to mean a linear or branched saturated hydrocarbon chain wherein the chain has from one to four carbon atoms, such as methyl, ethyl, n-propyl, isopropyl, n-butyl, isobutyl, sec-butyl and tert-butyl.

The oligomer of the invention, such as the antisense oligonucleotide, may comprise more than one type of LNA unit. Suitably, the compound may comprise both beta-D-oxy-LNA, and one or more of the following LNA units: thio-LNA, amino-LNA, oxy-LNA, ena-LNA and/or alpha-LNA in either the D-beta or L-alpha configurations or combinations thereof.

Benefits of utilising LNA, and methods of preparing and purifying LNA and LNA oligonucleotides are disclosed in PCT/DK2006/000512 which are hereby incorporated by reference.

In one embodiment, the oligomer of the invention does not comprise any RNA units.

In one embodiment, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

RNAse H Recruitment and Gapmer Oligonucleotides.

The oligomer of the invention is a gapmer of formula A-B-C, or optionally A-B-C-D or D-A-B-C.

Region A may consist of 1, 2, 3, 4, 5 or 6 contiguous LNA units; region B may consist of 6, 7, 8, 9, 10, 11 or 12 nucleotide units, such as DNA units, or a combination of DNA and other units capable of recruiting RNAseH, such as alpha-L LNA units.

In one embodiment, the oligomer comprises 2, 3, 4, 5 or 6 LNA units (i.e. the total of LNA units in regions A and C. In one embodiment at least one of region A and/or C consists of 2 LNA units. In one embodiment, region A and C both consist of 2 LNA units. In one embodiment A consists of 1 LNA unit. In one embodiment A consists of 2 LNA units. In one embodiment A consists of 3 LNA units. In one embodiment C consists of 1 LNA unit. In one embodiment C consists of 2 LNA units. In one embodiment C consists of 3 LNA units. In one embodiment B consists of 7 nucleobase units. In one embodiment B consists of 8 nucleobase units. In one embodiment B consists of 9 nucleobase units. In one embodiment B consists of 10 nucleobase units. In one embodiment A and/or C consists of 4 or 5 nucleobase units. In one embodiment B comprises of between 1-9 DNA units, such as 2, 3, 4, 5, 6, 7 or 8 DNA units. In one embodiment B consists of only DNA units—i.e. 7, 8 or) DNA units (2' deoxyribonucleoside). In one embodiment B comprises of at least one LNA unit which is in the alpha-L configuration, such as 2, 3, 4, 5, 6, 7, 8 or 9 LNA units in the alpha-L-configuration. In one embodiment B comprises of at least one alpha-L-oxy LNA unit or wherein all the LNA units in the alpha-L-configuration are alpha-L-oxy LNA units. In one embodiment the number of nucleobases in A-B-C are selected from the group consisting of: 1-8-1, 1-8-2, 2-8-1, 2-8-2, 3-8-3, 2-8-3, and 3-8-2. In one embodiment the number of nucleobases in A-B-C are selected from the group consisting of: 3-9-3, 3-10-3, 4-8-3, or 3-8-4. In one embodiment the number of nucleobases in A-B-C are selected from the group consisting of: 1-9-1, 1-9-2, 2-9-1, 2-9-2, 3-9-2, and 2-9-3. In one embodiment the number of nucleobases in A-B-C are selected from the group consisting of: 2-7-1, 1-7-2, 2-7-2, 3-7-3, 2-7-3, 3-7-2, 3-7-4, and 4-7-3. In one embodiment A and C both consist of two LNA units each, and B consists of 8 nucleobase units, preferably DNA units. In one embodiment the LNA units of A and C are independently selected from oxy-LNA, thio-LNA, and amino-LNA, in either of the beta-D and alpha-L configurations or combinations thereof. In one embodiment LNA units of A and C are beta-D-oxy-LNA. In one embodiment A consists of 2 LNA units neither of which are alpha-L-oxy LNA. In one embodiment C consists of 2 LNA units neither of which are alpha-L-oxy LNA. In one embodiment A does not comprise any thio-LNA nucleobases. In one embodiment C does not comprise any thio-LNA nucleobases. In one embodiment A does not comprise any amino-LNA nucleobases. In one embodiment C does not comprise any amino-LNA nucleobases. When present, D typically consists of a single DNA unit. In one embodiment, there is no region D. In one embodiment regions A and C consist of either 1 or 2 nucleobase units. In one embodiment, region C consists of 2 residues, and region A consists of 1, 2 or 3 nucleobase units. In one embodiment, region A consists of 2 residues, and region C consists of 1, 2 or 3 nucleobase units.

In one embodiment the 3' and/or 5' residues of region B are an LNA nucleobase in the alpha L configurations, such as alpha-L-oxy LNA. In one embodiment, which may be the same of different, at least one of the nucleobase units other than the 3' and/or 5' residues of region B are an LNA nucleobase in the alpha L configurations, such as alpha-L-oxy LNA.

Region B is essential in terms of recruitment of RNAseH—it is therefore highly preferred that region B comprises a nucleobase sequence that is capable of recruiting RNAseH. DNA nucleotides are highly preferred, although as disclosed in WO2004/046160, a DNA unit (or more) in region B may be substituted with one (or more) LNA units which are in the alpha-L configuration, particularly preferred being alpha-L-oxy LNA. Suitably 1, 2, 3, 4, 5, 6, 7, 8 or 9 of the DNA units of region B may be substituted in this manner, although when such substitutions are made it is recommended that, for example only 1, 2, or 3 of such substitutions are made in region B.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

As referred to above, one or more of the DNA nucleotides in the central domain (B) may be substituted with one or more nucleotide analogues which are capable of recruiting RNAse H, or even all the DNA nucleotides may be substituted with nucleotide analogues which are capable or recruiting RNAse H. LNA nucleobases which form the alpha-L configuration, such as alpha-L-oxy LNA are particularly preferred nucleotide analogues which may be incorporated into region B as they are capable of recruiting RNAseH. In this respect region B may comprise both alpha-L-LNA and DNA units. Region B may comprise an alpha-L-LNA unit, which may, for example, be at position 1, 2, 3, 4, 5, 6, 7, 8, or 9 of region B (as determined from either the 3' or 5' end), and in one embodiment the remaining nucleobases of region B may be DNA, or alternatively region B may comprise one or more further alpha-L-LNA units, such as 2, 3, 4, 5, 6, 7, 8, or 9 further alpha-L-LNA units. In one embodiment, region B comprises 2 alpha-L-LNA units, and the remaining nucleobase units are DNA. In a further embodiment, region B comprises 3 alpha-L-LNA units, and the remaining nucleobase units are DNA. The alpha-L-units may, in one embodiment be positioned at the 5' and or 3' positions of region B, and/or in a non terminal position of region B. Where more than one alpha-L-LNA unit is present in region B, region B may comprise a sequence where the alpha-LNA units are either adjacent to each other (i.e. ant least 5'-LNA-LNA-3') and/or where the alpha LNA units are non-adjacent, i.e. separated by at least 1, such as 1, 2, 3, 4, 5, 6, 7, 8, 9 or 10 alternative nucleobases or nucleotides, such as DNA units.

In one embodiment, the gapmer, of formula A-B-C, further comprises a further region, D, which consists or comprises, preferably consists, of one DNA sugar residue terminal of the 3' region (C) of the oligomeric compound. Alternatively, region D may be immediately 5' (i.e. adjacent to) to region A.

Preferably the LNA units of the oligomer, such as an antisense oligonucleotide, of the invention are selected from one or more of the following: thio-LNA, amino-LNA, oxy-LNA, ena-LNA and/or alpha-LNA in either the D-beta or L-alpha configurations or combinations thereof. Beta-D-oxy-LNA is a preferred LNA for use in the oligomer of the invention, particularly in regions A and C (where as alpha-L-LNA are preferred, when present, in region B). Thio-LNA may also be preferred for use in the oligomer of the invention. Amino-LNA may also be preferred for use in the oligomer of the invention. Oxy-LNA may also be preferred for use in the oligomer of the invention. Ena-LNA may also be preferred for use in the oligomer of the invention. Alpha-LNA may also be preferred for use in the oligomer of the invention.

Internucleobase/Internucleoside Linkages

The terms "linkage group" or "Internucleoside linkage" or "Internucleobase linkage" are intended to mean a group capable of covalently coupling together two nucleotides, two nucleotide analogues, and a nucleotide and a nucleotide analogue, etc. Specific and preferred examples include phosphate groups and phosphorothioate groups.

Suitable internucleoside linkages include those listed within PCT/DK2006/000512, for example the internucleoside linkages listed on the first paragraph of page 34 of PCT/DK2006/000512 (hereby incorporated by reference).

Suitable sulphur (S) containing internucleoside linkages as provided above may be preferred. Phosphorothioate internucleotide linkages are also preferred, particularly for the gap region (B). Phosphorothioate linkages may also be used for the flanking regions (A and C, and for linking C to D, and D). Regions A, B and C, may however comprise internucleoside linkages other than phosphorothioate, such as phosphodiester linkages, particularly, for instance when the use of nucleotide analogues protects the internucleoside linkages within regions A and C from endo-nuclease degradation.

The internucleobase linkages in the oligomer may be phosphodiester, phosphorothioate or boranophosphate so as to allow RNase H cleavage of targeted RNA. Phosphorothioate is preferred, for improved nuclease resistance and other reasons, such as ease of manufacture.

In one embodiment, the internucleoside linkages are independently selected from the group consisting of: phosphodiester, phosphorothioate and boranophosphate.

In one embodiment, the oligomer comprises at least one phosphorothioate internucleoside linkage. In one embodiment, the internucleoside linkages adjacent to or between DNA units are phosphorothioate linkages. In one embodiment, the linkages between at least one pair, such as two (independent or consecutive)pairs, of consecutive LNA units, such as 2 LNA units in region A or C, is a phosphodiester linkage. In one embodiment, the linkages between consecutive LNA units such as 2 LNA units in region A and/or C, are phosphodiester linkages. In one embodiment, all the internucleoside linkages, or the remaining internucleoside linkages, are phosphorothioate linkages. In some embodiments region A comprises at least one phosphodiester linkage between two nucleotide analogue units, or a nucleotide analogue unit and a nucleobase unit of Region B. In some embodiments region C comprises at least one phosphodiester linkage between two nucleotide analogue units, or a nucleotide analogue unit and a nucleobase unit of Region B. In some embodiments, region C comprises at least one phosphodiester linkage between a nucleotide analogue unit and a nucleobase unit of Region D. In some embodiments, region A comprises at least one phosphodiester linkage between a nucleotide analogue unit and a nucleobase unit of region D. In some embodiments the linkage between the 3' nucleotide analogue of region A and the 5' nucleobase of region B is a phosphodiester. In some embodiments the linkage between the 3' nucleobase of region B and the 5' nucleotide analogue of region C is a phosphodiester. In some embodiments the linkage between the two adjacent nucleotide analogues at the 5' end of region A are phosphodiester. In some embodiments the linkage between the two adjacent nucleotide analogues at the 3' end of region C is phosphodiester. In some embodiments the linkage between the two adjacent nucleotide analogues at the 3' end of region A is phosphodiester. In some embodiments the linkage between the two adjacent nucleotide analogues at the 5' end of region C is phosphodiester. In some embodiments all the linkage s between nucleotide analogues present in the compound of the invention are phosphodiester. In some embodiments, such as the embodiments referred to above, where suitable and not specifically indicated, all remaining linkage s are either phosphodiester or phosphorothioate, or a mixture thereof, preferably phosphorothioate. In one embodiment the only phosphodiester linkages are found within regions A and/or C, or between regions A-B and/or C-B.

When referring to specific gapmer oligonucleotide sequences, such as those provided herein it will be understood that, in one embodiment, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5'methyl modified cytosine, in one embodiment, one or more of the Cs present in the oligonucleotide may be unmodified C residues.

Phosphodiester/Phosphorothioate Chimeras

The present inventors have found that the introduction of a single phosphodiester into a gapmer can enhance the bioavailability of the oligomer in vivo. Furthermore, the present inventors have found that the introduction of a single phosphodiester into a gapmer can result in an enhanced accumulation of the oligomer in kidney cells, particularly kidney cortex cells. Suitably, the enhanced distribution to the kidney cells may be seen when comparing the relative amounts which accumulate in the liver and the kidney. Suitably, as described herein, one or two further phosphodiester linkages may be found.

The use of oligonucleotides of between 10-16 nucleobases in length, such as shortmers, is, in many instances, advantageous as they have enhanced in vivo bioavailability due to their small size. However, their small size also results in an increased risk of excretion in the kidney. The present inventors were therefore surprised to find that the introduction of a single phosphodiester linkage, or two phosphodieater linkages, in an otherwise phosphorothioate oligomer shortmer was sufficient to enhance the bioavailability and the accumulation rather than the excretion from the kidney. Suitably the phosphodiester linkages should preferably be placed (inserted) either between two adjacent nucleotide analogues, such as LNA, present in regions A and or C, and/or, in one embodiment, between an adjacent nucleotide analogue, such as LNA, present in regions A and or C, and a nucleobase of region B.

The present invention therefore also provides for a method for modifying a fully phosphorothioate oligomer to enhance its accumulation or bioavailability in an organ, such as the kidney said method comprising replacing a total of one or two of the phosphorothioate linkages with phosphodiester bonds.

It will be understood that by the term modifying, we refer to both a method of manufacture of oligomer and/or a method of designing. In this regards it is not considered that one should take a physical fully phosphorothioate oligomer and replace one or two of the phosphorothioate linkages with phosphodiester linkages, but, instead it is a method of designing modified phosphorothioate oligomers, by replacing one or two of the phosphorothioate linkages with phosphodiester linkages. Subsequently the oligomers can be made using routine oligonucleotide synthesis chemistry.

Whilst the present inventors consider that such modified oligomers are particularly useful for shortmer oligonucleotides, it is considered that the method is not limited to oligonucleotides of, say between 10-14 nucleobases, but is also applicable to longer oligomers, such as oligomers consisting of a contiguous nucleobase sequence of a total of 10-25 nucleobase units, such as 11, 12, 13, 14, 15, 16, 17, 18, 19, 20, 21, 22, 23, or 25 nucleobase units.

Conjugates

In the present context the term "conjugate" is intended to indicate a heterogenous molecule formed by the covalent attachment of a compound as described herein (i.e. a compound comprising a sequence of nucleotides analogues) to one or more non-nucleotide/non-nucleotide-analogue, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol. When the compound of the invention consists of a nucleobase sequence, it may, in one embodiment further comprise a non-nucleobase portion, such as the above conjugates.

The invention also provides for a conjugate comprising the compound of the invention and at least one non-nucleotide or non-polynucleotide moiety covalently attached to said compound. PCT/DK2006/000512 provides suitable ligands and conjugates, which are hereby incorporated by reference.

In one embodiment of the invention, the oligonucleotide may be linked to ligands/conjugates, which may be used, e.g. to increase the cellular uptake of the oligonucleotide. This conjugation can take place at the terminal positions 5'/3'-OH but the ligands may also take place at the sugars and/or the bases. The 3'-OH is preferred site for cholesterol conjugation.

In a preferred embodiment, the oligonucleotide of the invention is conjugated with a moiety which improvise the in vivo uptake, such as cholesterol.

Thus, the oligomeric compound may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the Oligomeric compound may be arranged in dimeric or dendritic structures.

In one embodiment referring to the conjugate, the non-nucleotide or non-polynucleotide moiety consists or comprise a sterol group such as cholesterol.

Other such non-nucleotide or non-polynucleotide moieties include, but are not limited to, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In one embodiment of the invention the oligomeric compound is linked to ligands/conjugates, which may be used, e.g. to increase the cellular uptake of antisense oligonucleotides. PCT/DK2006/000512 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in one embodiment where the compound of the invention consists of a specified nucleic acid, as herein disclosed, the compound may also comprise at least one non-nucleotide or non-polynucleotide moiety (e.g. not comprising one or more nucleotides or nucleotide analogues) covalently attached to said compound.

Applications

The oligomers of the invention may be utilized as research reagents for, for example, diagnostics, therapeutics and prophylaxis.

In research, such oligomers may be used to specifically inhibit the synthesis of the target protein (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate the target expression in cell and tissues by Northern blotting, in-situ hybridisation or similar techniques.

For therapeutics, an animal or a human, suspected of having a disease or disorder, which can be treated by modulating the expression of the target—is treated by administering antisense compounds (oligomers) in accordance with this invention. Further provided are methods of treating an animal, such as a mouse or rat, or preferably, treating a human, suspected of having or being prone to a disease or condition, associated with expression of the target by administering a therapeutically or prophylactically effective amount of one or more of the oligomers or compositions of the invention.

The pharmaceutical composition according to the invention may be used for the treatment of conditions associated with:

ApoB-100 targeting oligomers—abnormal levels of apoB-100, atherosclerosis, hypercholesterolemia or hyperlipidemia. It will be recognised that the ApoB-100 targeting oligomers may be combined with further therapeutic agents in the pharmaceutical composition according to the invention—such as those further therapeutic agents provided in U.S. 60/896,419 and/or WO2007/031081—hereby incorporated by reference.

Hif-1alpha targeting oligomers—abnormal levels of Hif-1alpha—artherosclerosis, psoriasis, diabetic retinopathy, macular degeneration, rheumatoid arthritis, asthma, inflammatory bowel disease, warts, allergic dermatitis, inflammation, and skin inflammation. It will be recognised that the Hif-1alpha targeting oligomers may be combined with further therapeutic agents in the pharmaceutical composition according to the invention—such as those further therapeutic agents provided in WO2006/050734—hereby incorporated by reference.

Suitable dosages, formulations, administration routes, compositions, dosage forms, combinations with other therapeutic agents, pro-drug formulations are also provided in PCT/DK2006/000512—which are hereby incorporated by reference.

The invention also provides for a pharmaceutical composition comprising a compound or a conjugate as herein described or a conjugate, and a pharmaceutically acceptable diluent, carrier or adjuvant. PCT/DK2006/000512 provides suitable and preferred pharmaceutically acceptable diluent, carrier and adjuvants—which are hereby incorporated by reference.

Pharmaceutical Application

The pharmaceutical application of LNA oligomers is, for example, described in WO2007/031081 (anti-ApoB oligomers) and WO2006/050734 (anti-hif1-alpha oligomers).

Embodiments

The following further embodiments may be combined with the features of the invention as referred to herein:

1. An oligomer consisting of a contiguous nucleobase sequence of a total of 10, 11, 12, 13 or 14 nucleobase units, wherein the contiguous nucleobase sequence is of formula (5'-3'), A-B-C, wherein: A consists of 1, 2 or 3 LNA units; B consists of 7, 8 or 9 contiguous nucleobase units which are capable of recruiting RNAseH when formed in a duplex with a complementary RNA molecule (such as a mRNA target); and C consists of 1, 2 or 3 LNA units.
2. The oligomer according to embodiment 1, wherein A consists of 1 LNA unit.
3. The oligomer according to embodiment 1, wherein A consists of 2 LNA units.
4. The oligomer according to embodiment 1, wherein A consists of 3 LNA units.
5. The oligomer according to any one of embodiments 1-4, wherein C consists of 1 LNA unit.
6. The oligomer according to any one of embodiments 1-4, wherein C consists of 2 LNA units.
7. The oligomer according to any one of embodiments 1-5, wherein C consists of 3 LNA units.
8. The oligomer according to any one of embodiments 1-7, wherein B consists of 7 nucleobase units.
9. The oligomer according to any one of embodiments 1-7, wherein B consists of 8 nucleobase units.
10. The oligomer according to any one of embodiments 1-7, wherein B consists of 9 nucleobase units.
11. The oligomer according to any one of embodiments 1-10, wherein B comprises of between 1-9 DNA units, such as 2, 3, 4, 5, 6, 7 or 8 DNA units.
12. The oligomer according to embodiment 11, wherein B consists of DNA units.
13. The oligomer according to any one of embodiments 1-11, wherein B comprises of at least one LNA unit which is in the alpha-L configuration, such as 2, 3, 4, 5, 6, 7, 8 or 9 LNA units in the alpha-L-configuration.
14. The oligomer according to embodiment 13, wherein B comprises of at least one alpha-L-oxy LNA unit or wherein all the LNA units in the alpha-L-configuration are alpha-L-oxy LNA units.
15. The oligomer according to any one of embodiments 1-14, wherein the number of nucleobases in A-B-C are selected from the group consisting of: 1-8-2, 2-8-1, 2-8-2, 3-8-3, 2-8-3, 3-8-2.
16. The oligomer according to any one of embodiments 1-15, wherein both A and C both consist of two LNA units each, and B consists of 8 nucleobase units, preferably DNA units.
17. The oligomer according to any one of embodiments 1-16, wherein the LNA units of A and C are independently selected from oxy-LNA, thio-LNA, and amino-LNA, in either of the beta-D and alpha-L configurations or combinations thereof.
18. The oligomer according to embodiment 17, wherein the LNA units of A and C are beta-D-oxy-LNA.
19. The oligomer according to any one of embodiments 1-18, wherein A consists of 2 LNA units neither of which are alpha-L-oxy LNA.
20. The oligomer according to any one of embodiments 1-19, wherein C consists of 2 LNA units neither of which are alpha-L-oxy LNA.
21. The oligomer according to any one of embodiments 1-20, wherein A does not comprise any thio-LNA nucleobases.
22. The oligomer according to any one of embodiments 1-21, wherein C does not comprise any thio-LNA nucleobases.
23. The oligomer according to any one of embodiments 1-22, wherein A does not comprise any amino-LNA nucleobases.
24. The oligomer according to any one of embodiments 1-23 wherein C does not comprise any amino-LNA nucleobases.
25. The oligomer according to any one of embodiments 1-24, wherein the internucleoside linkages are independently selected from the group consisting of: phosphodiester, phosphorothioate and boranophosphate.
26. The oligomer according to embodiment 25, wherein the oligomer comprises at least one phosphorothioate internucleoside linkage.
27. The oligomer according to embodiment 25, wherein the internucleoside linkages adjacent to or between DNA units are phosphorothioate linkages.
28. The oligomer according to embodiment 26 or 27, wherein the linkages between at least one pair of consecutive LNA units, such as 2 LNA units in region A or C, is a phosphodiester linkage.
29. The oligomer according to embodiment 28, wherein all the linkages between consecutive LNA units such as 2 LNA units in region A and C, are phosphodiester linkages.
30. The oligomer according to embodiment 26 wherein all the internucleoside linkages are phosphorothioate linkages.
31. The oligomer according to any one of embodiments 1-30, wherein the contiguous nucleobase sequence is complementary to a corresponding region of a mammalian, such as a human mRNA, selected form the group consisting of ApoB-100, PCSK9, Hif1alpha, FABP4 and profilin.
32. The oligomer according to any one of embodiments 1-31, wherein the contiguous nucleobase sequence is selected from the group consisting of a contiguous nucleobase sequence present in, or corresponding to a nucleobase sequence of the oligomer sequences shown in any one of tables 1, 2, 3, 4, 5, 6, 7, 8, 9, 10 or 11.
33. A conjugate comprising the oligomer according to any one of the embodiments 1-32 and at least one non-nucleotide or non-polynucleotide moiety covalently attached to said compound.
34. A pharmaceutical composition comprising an oligomer as defined in any of embodiments 1-32 or a conjugate as defined in embodiment 33, and a pharmaceutically acceptable diluent, carrier, salt or adjuvant.
35. A pharmaceutical composition according to 34, wherein the oligomer is constituted as a pro-drug.
36. The use of an oligomer according to any one of embodiments 1-32 for the reduction in cellular concentration of a mRNA in a mammalian cell.
37. The use of an oligomer according to embodiment 36, wherein the mRNA is a human mRNA selected form the group consisting of ApoB-100, PCSK9, Hif1alpha, FABP4 and profilin.
38. A method for the reduction in the cellular concentration of a mRNA in a mammalian cell, said method comprising the administration of an oligomer according to any one of embodiments 1-32 to the mammalian cell, wherein said mammalian cell comprises an mRNA species which comprises a nucleobase sequence which is complementary to said oligomer.

EXAMPLES

Example 1

Monomer Synthesis

The LNA nucleotide analogue building blocks (e.g. β-D-oxy-LNA, β-D-thio-LNA, β-D-amino-LNA and α-L-oxy-LNA) can be prepared following established published procedures—for example see WO2007/031081, hereby incorporated by reference.

Example 2

Oligonucleotide Synthesis

Oligonucleotides were synthesized according to the method described and referenced in WO07/031,081.

Oligonucleotide Compounds

In SEQ ID NOS: 16-40, upper case letters indicates nucleotide analogue units and subscript "s" represents phosphorothioate linkage. Absence of "s" indicates phosphodiester linkage.

| Test substance | Sequence | Size | |
|---|---|---|---|
| SEQ ID NO: 1 | 5'-CAGC ATTG GTAT TCAG-3' | 16 | Antisense motif |
| SEQ ID NO: 2 | 5'-CAGC ATTG GTAT TCA-3' | 15 | Antisense motif |
| SEQ ID NO: 3 | 5'-AGCA TTGG TATT CAG-3' | 15 | Antisense motif |
| SEQ ID NO: 4 | 5'-CAGC ATTG GTAT TC-3' | 14 | Antisense motif |
| SEQ ID NO: 5 | 5'-AGCA TTGG TATT CA-3' | 14 | Antisense motif |
| SEQ ID NO: 6 | 5'-GCAT TGGT ATTC AG-3' | 14 | Antisense motif |
| SEQ ID NO: 7 | 5'-CAGC ATTG GTAT T-3' | 13 | Antisense motif |
| SEQ ID NO: 8 | 5'-AGCA TTGG TATT C-3' | 13 | Antisense motif |
| SEQ ID NO: 9 | 5'-GCAT TGGT ATTC A-3' | 13 | Antisense motif |

-continued

| Test substance | Sequence | Size | |
|---|---|---|---|
| SEQ ID NO: 10 | 5'-CATT GGTA TTCA G-3' | 13 | Antisense motif |
| SEQ ID NO: 11 | 5'-CAGC ATTG GTAT-3' | 12 | Antisense motif |
| SEQ ID NO: 12 | 5'-AGCA TTGG TATT-3' | 12 | Antisense motif |
| SEQ ID NO: 13 | 5'-GCAT TGGT ATTC-3' | 12 | Antisense motif |
| SEQ ID NO: 14 | 5'-CATT GGTA TTCA-3' | 12 | Antisense motif |
| SEQ ID NO: 15 | 5'-ATTG GTAT TCAG-3' | 12 | Antisense motif |
| SEQ ID NO: 16 | 5'-$A_sG_s^{Me}C_sa_st_st_sg_sg_st_sa_st_sT_s^{Me}C_sA_s$g-3' | 16 | Motif #1 |
| SEQ ID NO: 17 | 5'-$A_sG_s^{Me}C_sa_st_st_sg_sg_st_sa_st_sT_s^{Me}C_sA$-3' | 14 | Motif #5 |
| SEQ ID NO: 18 | 5'-$AG_s^{Me}C_sa_st_st_sg_sg_st_sa_st_sT_s^{Me}C_sA$-3' | 14 | Motif #5 |
| SEQ ID NO: 19 | 5'-$A_sG^{Me}C_sa_st_st_sg_sg_st_sa_st_sT_s^{Me}C_sA$-3' | 14 | Motif #5 |
| SEQ ID NO: 20 | 5'-$A_sG_s^{Me}Ca_st_st_sg_sg_st_sa_st_sT_s^{Me}C_sA$-3' | 14 | Motif #5 |
| SEQ ID NO: 21 | 5'-$A_sG_s^{Me}C_sa_st_st_sg_sg_st_sa_st_sT_s^{Me}C_sA$-3' | 14 | Motif #5 |
| SEQ ID NO: 22 | 5'-$A_sG_s^{Me}C_sa_st_st_sg_sg_st_sa_st_sT^{Me}C_sA$-3' | 14 | Motif #5 |
| SEQ ID NO: 23 | 5'-$A_sG_s^{Me}C_sa_st_st_sg_sg_st_sa_st_sT^{Me}_sCA$-3' | 14 | Motif #5 |
| SEQ ID NO: 24 | 5'-$AG_s^{Me}C_sa_st_st_sg_sg_st_sa_st_sT_s^{Me}CA$-3' | 14 | Motif #5 |
| SEQ ID NO: 25 | 5'-$AG^{Me}C_sa_st_st_sg_sg_st_sa_st_sT^{Me}CA$-3' | 14 | Motif #5 |
| SEQ ID NO: 26 | 5'-$G_s^{Me}C_sa_st_st_sg_sg_st_sa_st_sT_s^{Me}C_sA$-3' | 13 | Motif #9 |
| SEQ ID NO: 27 | 5'-$G^{Me}C_sa_st_st_sg_sg_st_sa_st_sT_s^{Me}C_sA$-3' | 13 | Motif #9 |
| SEQ ID NO: 28 | 5'-$G_s^{Me}Ca_st_st_sg_sg_st_sa_st_sT_s^{Me}C_sA$-3' | 13 | Motif #9 |
| SEQ ID NO: 29 | 5'-$G_s^{Me}C_sa_st_st_sg_sg_st_sa_st_sT_s^{Me}C_sA$-3' | 13 | Motif #9 |
| SEQ ID NO: 30 | 5'-$G_s^{Me}C_sa_st_st_sg_sg_st_sa_st_sT^{Me}C_sA$-3' | 13 | Motif #9 |
| SEQ ID NO: 31 | 5'-$G_s^{Me}C_sa_st_st_sg_sg_st_sa_st_sT^{Me}_sCA$-3' | 13 | Motif #9 |
| SEQ ID NO: 32 | 5'-$G^{Me}C_sa_st_st_sg_sg_st_sa_st_sT_s^{Me}CA$-3' | 13 | Motif #9 |
| SEQ ID NO: 33 | 5'-$G^{Me}C_sa_st_st_sg_sg_st_sa_st_sT^{Me}CA$-3' | 13 | Motif #9 |
| SEQ ID NO: 34 | 5'-$G_s^{Me}C_sa_st_st_sg_sg_st_sa_st_sT_s^{Me}C$-3' | 12 | Motif #13 |
| SEQ ID NO: 35 | 5'-$G^{Me}C_sa_st_st_sg_sg_st_sa_st_sT_s^{Me}C$-3' | 12 | Motif #13 |
| SEQ ID NO: 36 | 5'-$G_s^{Me}Ca_st_st_sg_sg_st_sa_st_sT_s^{Me}C$-3' | 12 | Motif #13 |
| SEQ ID NO: 37 | 5'-$G_s^{Me}C_sa_st_st_sg_sg_st_sa_st_sT_s^{Me}C$-3' | 12 | Motif #13 |
| SEQ ID NO: 38 | 5'-$G_s^{Me}C_sa_st_st_sg_sg_st_sa_st_sT^{Me}C$-3' | 12 | Motif #13 |
| SEQ ID NO: 39 | 5'-$G^{Me}C_sa_st_st_sg_sg_st_sa_st_sT^{Me}C$-3' | 12 | Motif #13 |
| SEQ ID NO: 40 | 5'-$G^{Me}Ca_st_st_sg_sg_st_sa_st_sT^{Me}C$-3' | 12 | Motif #13 |

Example 3

Cholesterol Levels in Plasma

Total cholesterol level is measured in plasma using a colometric assay Cholesterol CP from ABX Pentra. The cholesterol is measured following enzymatic hydrolysis and oxidation. 21.5 µL water was added to 1.5 µL plasma. 250 µL reagent is added and within 5 min the cholesterol content is measured at a wavelength of 540 nM. Measurements on each animal was made in duplicates. The sensitivity and linearity was tested with 2 fold diluted control compound (ABX Pentra N control). The relative Cholesterol level was determined by subtraction of the background and presented relative to the cholesterol levels in plasma of saline treated mice.

Example 4

Measurements of mRNA Levels

Antisense modulation of Apo-B100 expression can be assayed in a variety of ways known in the art. For example, Apo-B100 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially iQ Multi-Color Real Time PCR Detection System available from BioRAD. Real-time Quantitative PCR is a technique well known in the art and is taught in for example Heid et al. Real time quantitative PCR, Genome Research (1996), 6: 986-994.

Example 5

Screening of Oligonucleotides Targeting ApoB-100 mRNA (Dosing 3*5 mg/kg)

In this study 5 mg/kg/dose were dosed on 3 consecutive days (one dose/day i.v.) and animals were sacrificed 24 hours after last dosing. At sacrifice, liver and retro orbital sinus blood was sampled. Serum was prepared from blood for analysis of cholesterol. RNA was isolated from the liver and the expression of ApoB-100 mRNA was measured.

The effect of dosing three doses at 5 mg/kg/dose of oligoes of different length on ApoB-100 mRNA expression is shown in FIG. 1. SEQ ID NO 16 down regulated ApoB-100 mRNA with about 25-30%, whereas the 14-mer SEQ ID NO 17 and 12-mer SEQ ID NO 34 was much more potent and equally potent—down regulated ApoB-100 mRNA with about 75% after dosing 3 times 5 mg/kg.

Figure 2:
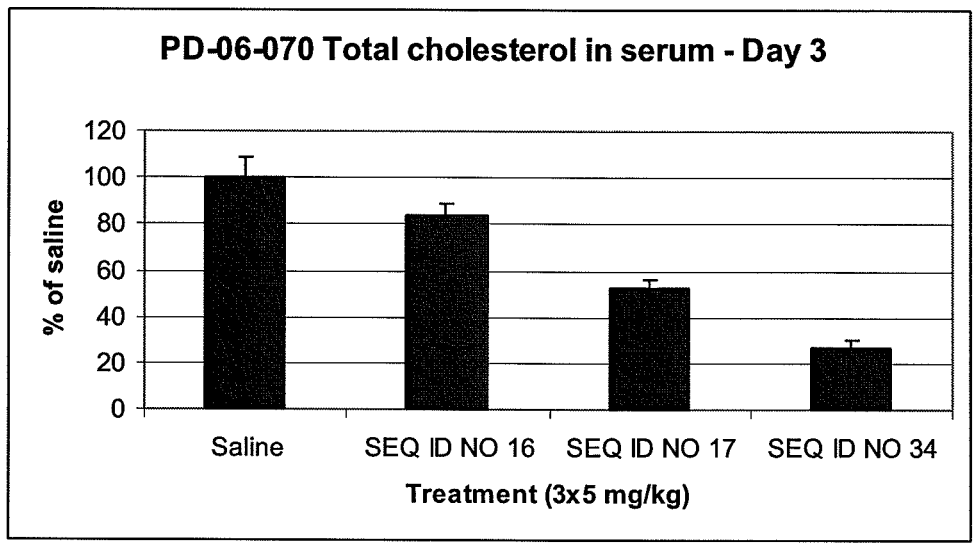
FIG. 2. Serum cholesterol levels at sacrifice (day 3) after dosing oligos of different length.

Total cholesterol was measured in serum at sacrifice, day 3 (FIG. 2). Similar to the results from the qPCR the best or the most potent effect was obtained with the 12-mer SEQ ID NO 34 followed by the 14-mer SEQ ID NO 17. The 16-mer (SEQ ID NO 16) reduced total cholesterol with about 18%.

Example 6

Dose Response and Duration of Action of SEQ ID NO 17 and SEQ ID NO 34 in C57BL/6 Female Mice In this study three different concentrations (10, 15 and 25 mg/kg) of SEQ ID NO 17 and SEQ ID NO 34 were examined for duration of action on ApoB-100 mRNA expression and serum cholesterol level. SEQ ID NO 17 and SEQ ID NO 34 were given as a single dose of 10, 15 or 25 mg/kg to C57BL/6 female mice. Mice were sacrificed at different time points (1, 3, 5 and 8 days) after dosing; liver and serum were examined for ApoB-100 mRNA expression, liver oligonucleotide concentration and cholesterol and ALT, respectively.

Analysis of Target mRNA Down Regulation

Figure 3:
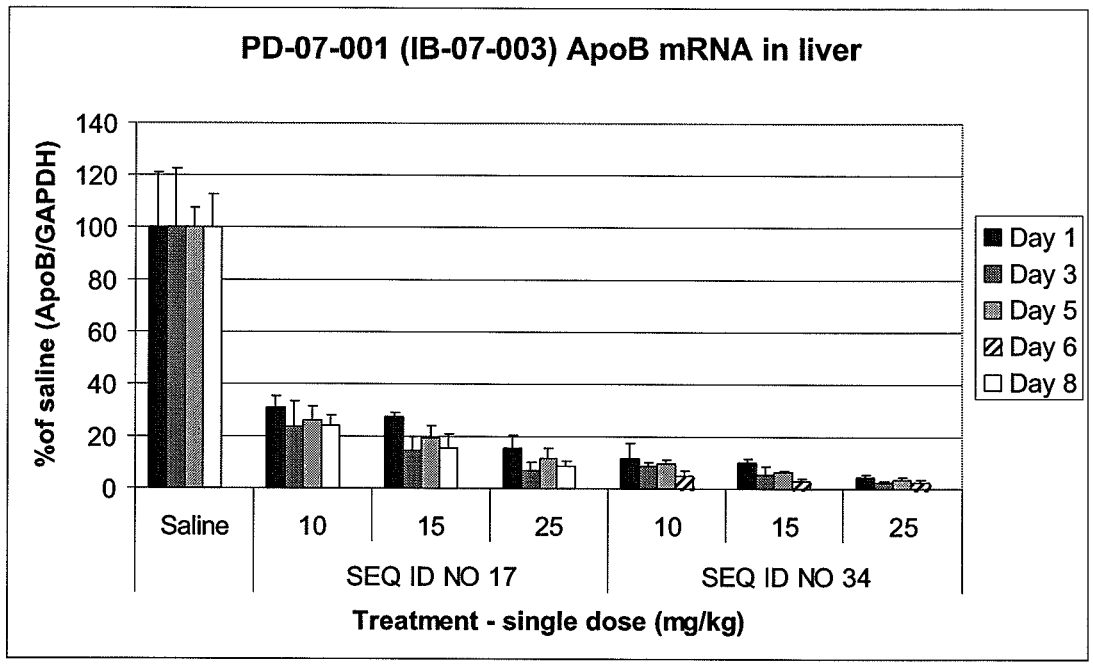
FIG. 3. The apoB-100 mRNA expression was measured by qPCR normalized to the house keeping gene GAPDH and presented relative to the saline group. Mice (n=5) were dosed once and sacrifice different days after dosing, liver was isolated and analyzed.

Liver sampled at sacrifice was analysed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 3). Twenty-four hours after dosing, down regulation of 90-95% was obtained with SEQ ID NO 34, whereas dosing of SEQ ID NO 17 resulted in 70-85% lower ApoB mRNA levels than in the saline control group.

Serum Cholesterol

Figure 4:
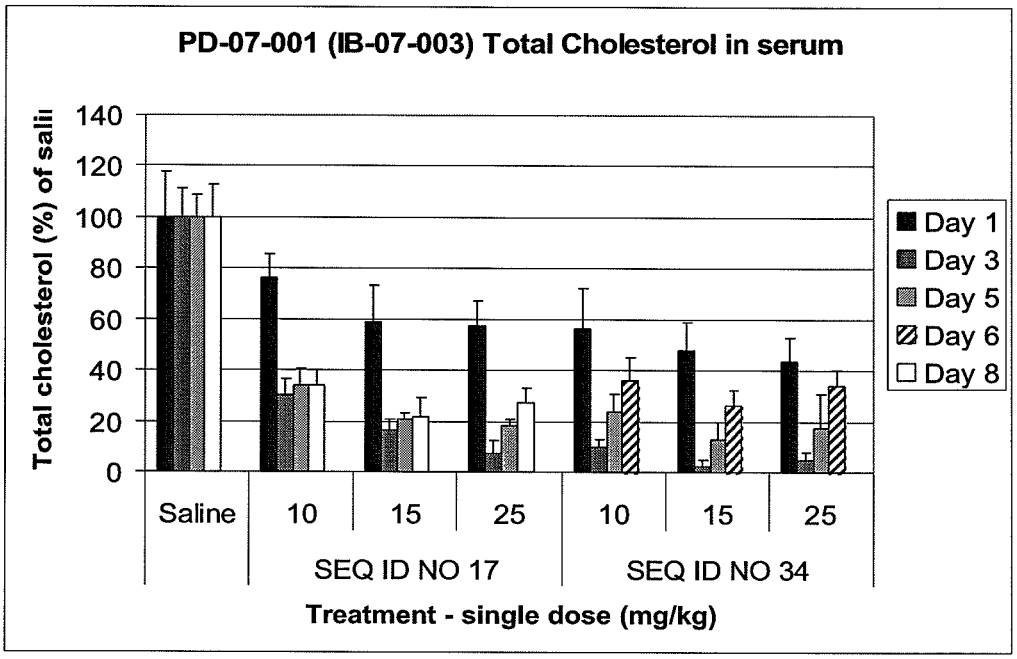
FIG. 4. Serum total cholesterol measured at sacrifice (days 1, 3, 5, 6 and 8) using a ABX pentra kit., n=5.

Blood serum used to measure cholesterol was sampled at sacrifice. Twenty-four hours after dosing SEQ ID NO 17 serum total cholesterol was reduced 25-40%, and dosing SEQ ID NO 34 gave 40-55% reduction in total cholesterol. At day 3, the total cholesterol level was further reduced: SEQ ID NO 17 gave 70-90% reduction in a dose dependent manner after doing 10, 15 or 25 mg/kg. SEQ ID NO 34 reduced total cholesterol with 90-95% relative to the saline control group. At day 5-8 the total cholesterol level increased in all groups except the group dosed SEQ ID NO 17 at 10 mg/kg. (FIG. 4).

Example 7

Dose Response and Duration of Action of SEQ ID NO 17 and SEQ ID NO 34 in C57BL/6 Female Mice A single dose of SEQ ID NO 17 and SEQ ID NO 34 at different concentrations was administered to C57BL/6J mice to find ED50 values for cholesterol. Duration of action was also included in this study, because we previously have seen that maximum effect of a single dose not always was achieved 24 hours after dosing. In Example 6, we completely down-regulated ApoB-100 mRNA after dosing 10, 15 or 25 mg/kg SEQ ID NO 34 and 25 mg/kg SEQ ID NO 17. In this study we therefore have chosen lower concentrations (1, 2.5 and 5 mg/kg).

Analysis of Target mRNA Down Regulation

Figure 5:
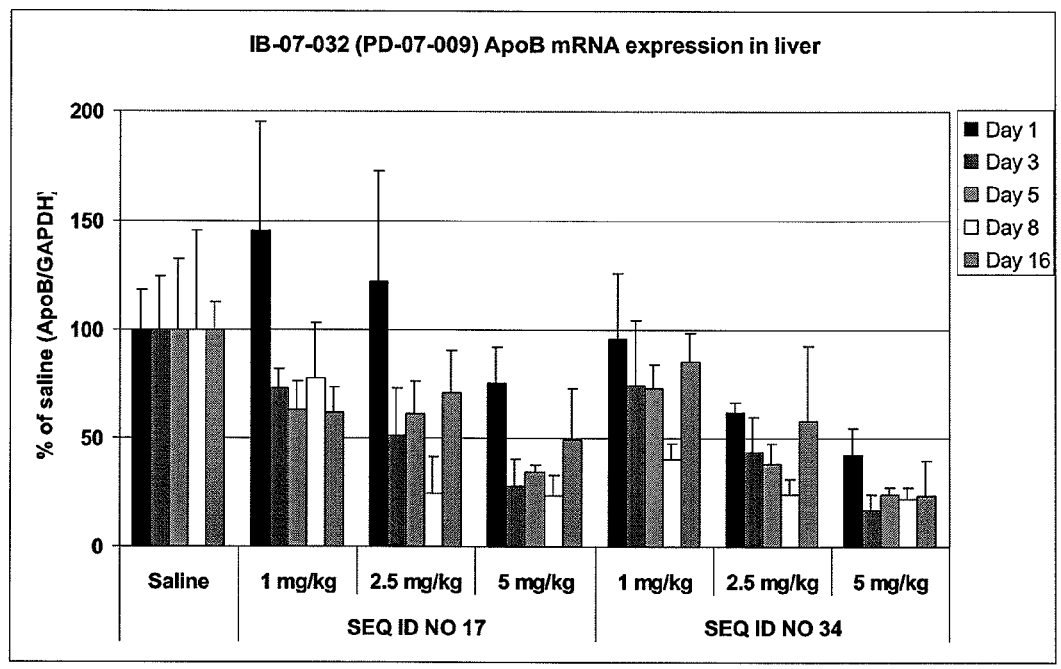
FIG. 5. The apoB-100 mRNA expression was measured by qPCR normalized to the house keeping gene GAPDH and presented relative to the saline group. Mice (n=5) were dosed once and sacrifice different days after dosing, liver was isolated and analyzed.
Figure 6:
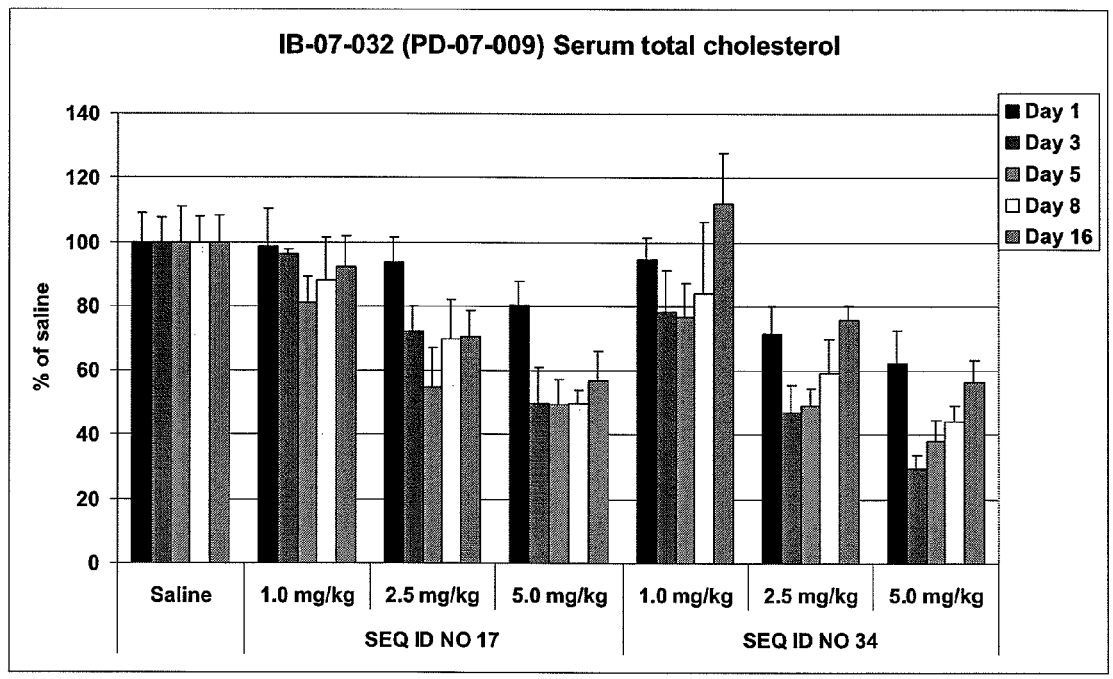
FIG. 6. Serum total cholesterol measured at sacrifice (days 1, 3, 5, 6, 8 and 16) using a ABX pentra kit., n=5.

Liver sampled at sacrifice was analysed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 5). A single dose of SEQ ID NO 17 of 1, 2.5 or 5 mg/kg resulted in a dose dependent down regulation of ApoB-100 mRNA with a duration of 5 days. Similar results were obtained with SEQ ID NO 34. At day 8 both oligonucleotides resulted in ApoB-100 mRNA expression that was similar after dosing 2.5 SEQ ID NO 34 and 5 mg/kg SEQ ID NO 17, reduction of 75%. At day 16 the mRNA level had increased again in all groups, except after dosing 5 mg/kg SEQ ID NO 34 with ApoB-100 mRNA down regulation of 75% similar to that at days 5 and 8.

Serum Cholesterol

Blood serum was sampled at sacrifice and used to measure cholesterol. The serum total cholesterol level reflected the mRNA expression of ApoB-100; dose dependent reduction with best effect at 5 days after dosing SEQ ID NO 17 at 1 and 2.5 mg/kg and similar effect at days 3, 5 and 8 after dosing 5 mg/kg (50% reduction). Dose dependent effect was also obtained after dosing SEQ ID NO 34 with best effect at day 3 after dosing 5 mg/kg (70% reduction) with following increase in cholesterol level (60% reduction at day 8 and 45% at day 16). However, the cholesterol levels in the groups dosed SEQ ID NO 34 did not follow the mRNA reductions in the groups dosed 2.5 and 5 mg/kg, e.g. dosing 5 mg/kg gave about 75% down regulation of ApoB-100 mRNA days 5-16 whereas the cholesterol level after dosing 2.5 mg/kg and 5 mg/kg increased from day 3 to day 16 from a 70% reduction to 45% reduction.

Example 8

Screening of Oligonucleotides Targeting ApoB-100 mRNA (Dosing 3*1 or 5 mg/kg i.v. Three Consecutive Days)

Figure 7:
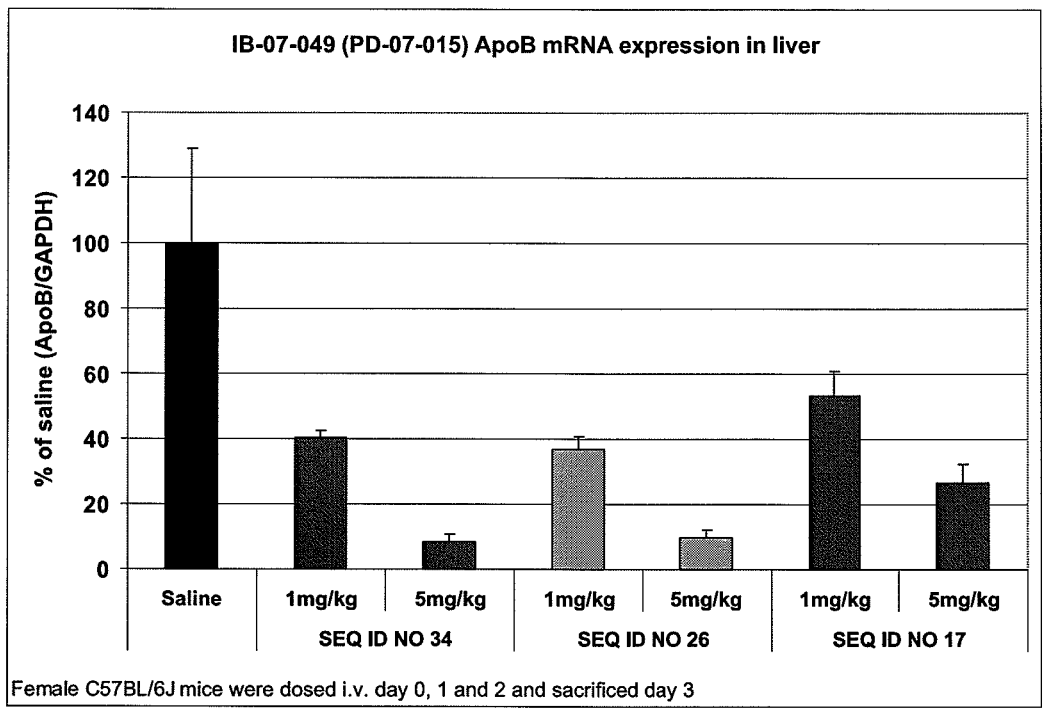
FIG. 7. The apoB-100 mRNA expression was measured by qPCR normalized to the house keeping gene GAPDH and presented relative to the saline group. Mice (n=5) were dosed 1 or 5 mg/kg 3 consecutive days and sacrificed 24 hours after last dosing (day 3), liver was isolated and analyzed.
Figure 8:
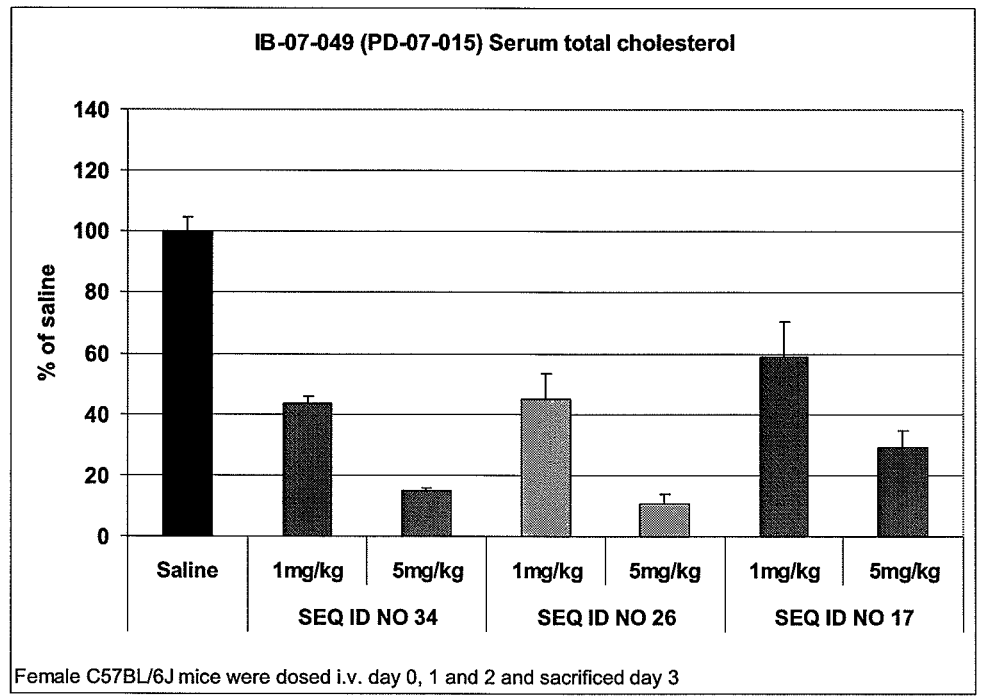
FIG. 8. Serum total cholesterol measured at sacrifice (day 3) using a ABX pentra kit., n=5.

The effect on ApoB-100 mRNA was examined at different days after dosing 1.0 or 5.0 mg/kg (one dose day 0) of the three LNA antisense oligonucleotides 12-mer SEQ ID NO 34, SEQ ID NO 26 13-mer and 14-mer SEQ ID NO 17 all targeting ApoB mRNA.
Analysis of Target mRNA Down Regulation
Liver sampled at sacrifice was analysed for ApoB-100 mRNA expression by qPCR. Data was normalized to Gapdh and presented relative to the data obtained by dosing saline. Dosing 3*1 or 5 mg/kg of SEQ ID NO 34, SEQ ID NO 17 or SEQ ID NO 26 was very effective to down regulate ApoB-100 mRNA in liver (FIG. 7). Dosing 1 mg/kg SEQ ID NO 34 or SEQ ID NO 26 down regulated ApoB-100 mRNA with 60% and 5 mg/kg resulted in 90% down regulation similar for both compounds. SEQ ID NO 17 dosed 3*1 mg/kg/dose or 5 mg/kg/dose down regulated target mRNA with 50% and 70% respectively.
Serum Cholesterol
At sacrifice blood for serum was sampled and used to measure cholesterol. Similar to the results for the mRNA expression, the SEQ ID NO 34 and SEQ ID NO 26 gave similar results: 60% reduction after dosing 3*1 mg/kg and about 85-90% after 3*5 mg/kg/dose. The SEQ ID NO 17 was a little less potent and reduced serum cholesterol with 40% and 70% after dosing 3*1 or 5 mg/kg/dose, respectively.

Example 9

Different Length (16-mer-10mer) and LNA Design of Oligonucleotides Targeting ApoB-100 mRNA (Dosing 3*5 mg/kg i.v. Three Consecutive Days)

Figure 9:
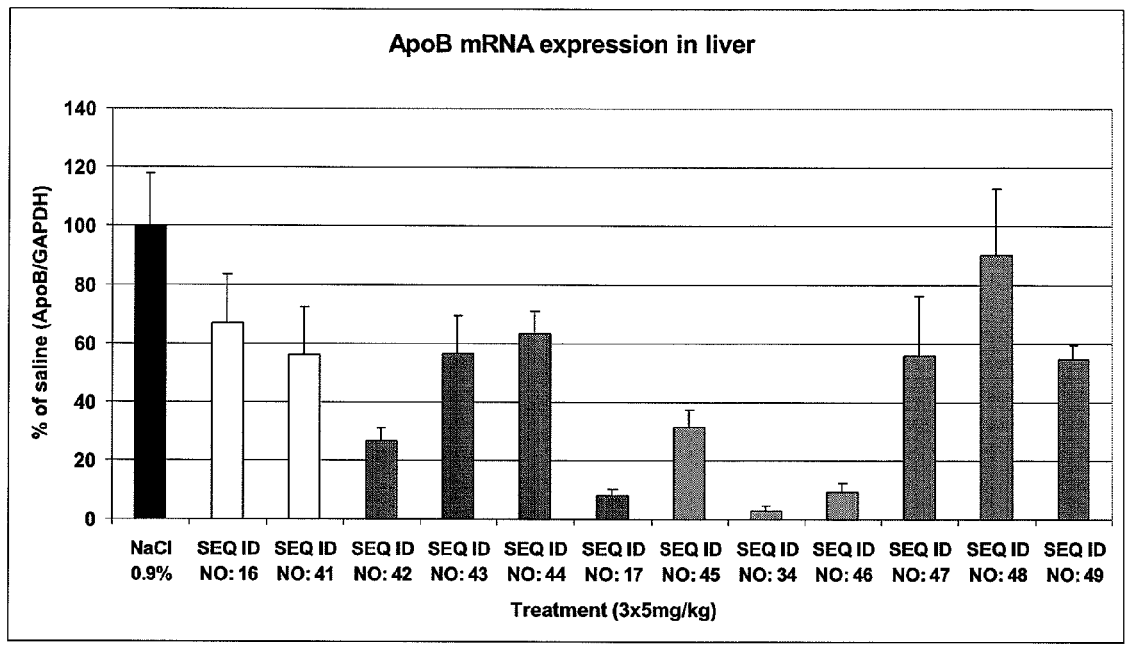
FIG. 9. The effect of dosing three doses at 5 mg/kg/dose of oligos of different length on ApoB-100 mRNA expression.

In this study 5 mg/kg/dose were dosed on 3 consecutive days (one dose/day i.v.) and animals were sacrificed 24 hours after last dosing. At sacrifice, liver was sampled. RNA was isolated from the liver and the expression of ApoB-100 mRNA was measured using qPCR.
The effect of dosing three doses at 5 mg/kg/dose of oligos of different length on ApoB-100 mRNA expression is shown in (FIG. 9). SEQ ID NO 16 and SEQ ID NO 41 down regulated ApoB-100 mRNA with about 35%-40%. Between the 14 mers SEQ ID NO 43 and SEQ ID NO 44 down regulated about 35%-40%, whereas the 14-mer SEQ ID NO 42 down regulated 70% and SEQ ID NO 17 down regulated 90%. Among the 12-mers SEQ ID NO 34 was the most potent of all the oligos in this study >90% down regulated whereas SEQ ID NO 45 and SEQ ID NO 46-down regulated ApoB-100 mRNA with about 70% and 90% respectively. 10 mers showed a maximum of 35%-40% down regulation.

Example 10

Different Length (16-mer-12mer) of Oligonucleotides Targeting ApoB-100 mRNA or Hif1-Alpha mRNA (dosing 3*5 mg/kg i.v. Three Consecutive Days)

Figure 10:
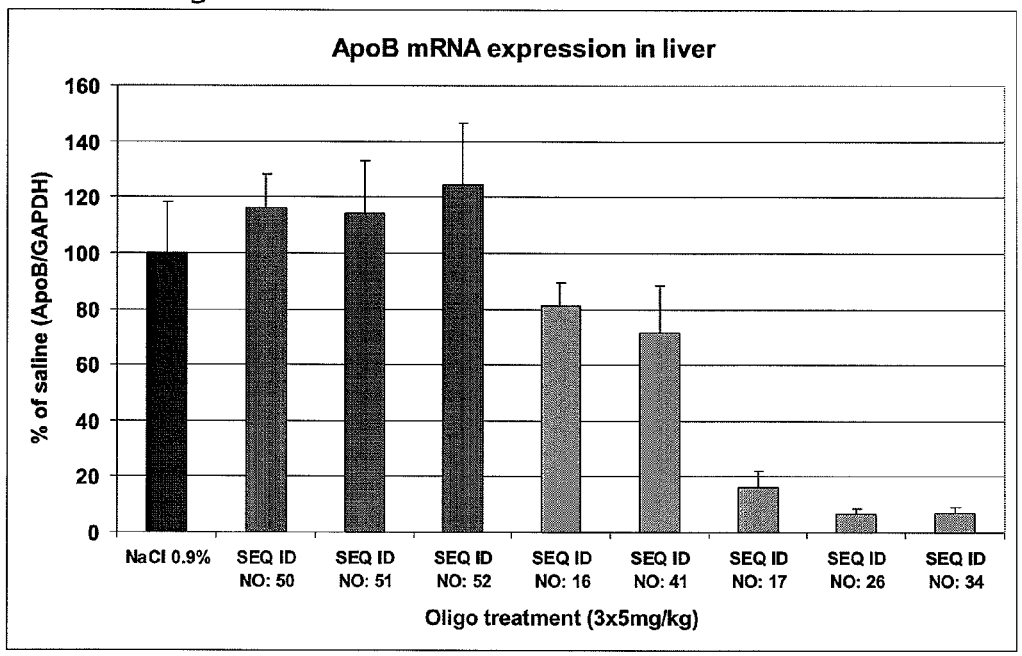
FIGS. 10 and 11. SEQ ID NOS 16, 41, 17, 26, 34 all against ApoB mRNA down regulated ApoB 30%, 30%, 80%, 90%, 90% respectively but had no effect on Hif1-alpha mRNA whereas SEQ ID NOs 50, 51 and 52 against Hif1-alpha down-regulated Hif1-alpha mRNA by 0%, 40% and 70% respectively but had no effect on ApoB mRNA.
Figure 11:
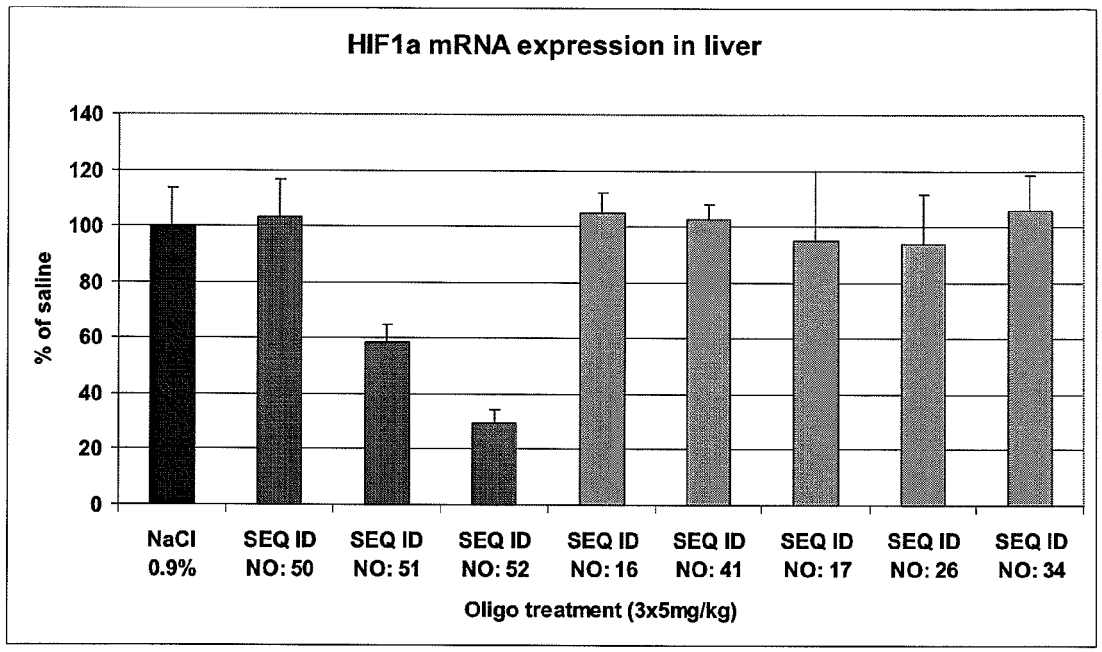
Figure 12:
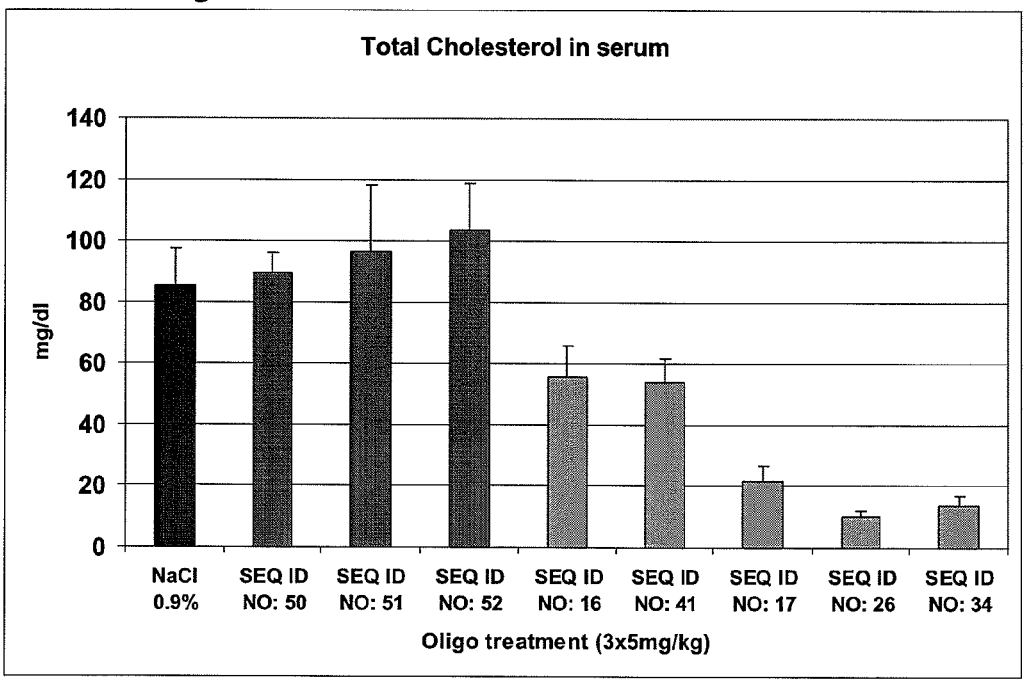
FIG. 12. SEQ ID NOS 16, 41, 17, 26, 34 all against ApoB mRNA down regulated serum cholesterol by 40%, 40%, 80%, 90%, 85% respectively whereas SEQ ID NO's 50, 51, 52 showed no effect on serum cholesterol.

In this study 5 mg/kg/dose were dosed on 3 consecutive days (one dose/day i.v.) and animals were sacrificed 24 hours after last dosing. At sacrifice, liver and retro orbital sinus blood was sampled. Serum was prepared from blood for analysis of cholesterol. RNA was isolated from the liver and the expression of ApoB-100 mRNA and Hif1-alpha was measured using qPCR.
SEQ ID NOS 16, 41, 17, 26, 34 all against ApoB mRNA down regulated ApoB 30%, 30%, 80%, 90%, 90% respectively but had no effect on Hif1-alpha mRNA (FIG. 10 and FIG. 11). SEQ ID NO's 50, 51 and 52 against Hif1-alpha down-regulated Hif1-alpha mRNA by 0%, 40% and 70% respectively but had no effect on ApoB mRNA (FIG. 10 and FIG. 11).
SEQ ID NOS 16, 41, 17, 26, 34 all against ApoB mRNA down regulated serum cholesterol by 40%, 40%, 80%, 90%, 85% respectively whereas SEQ ID NO's 50, 51, 52 showed no effect on serum cholesterol (FIG. 12).

Example 11

Figure 13:
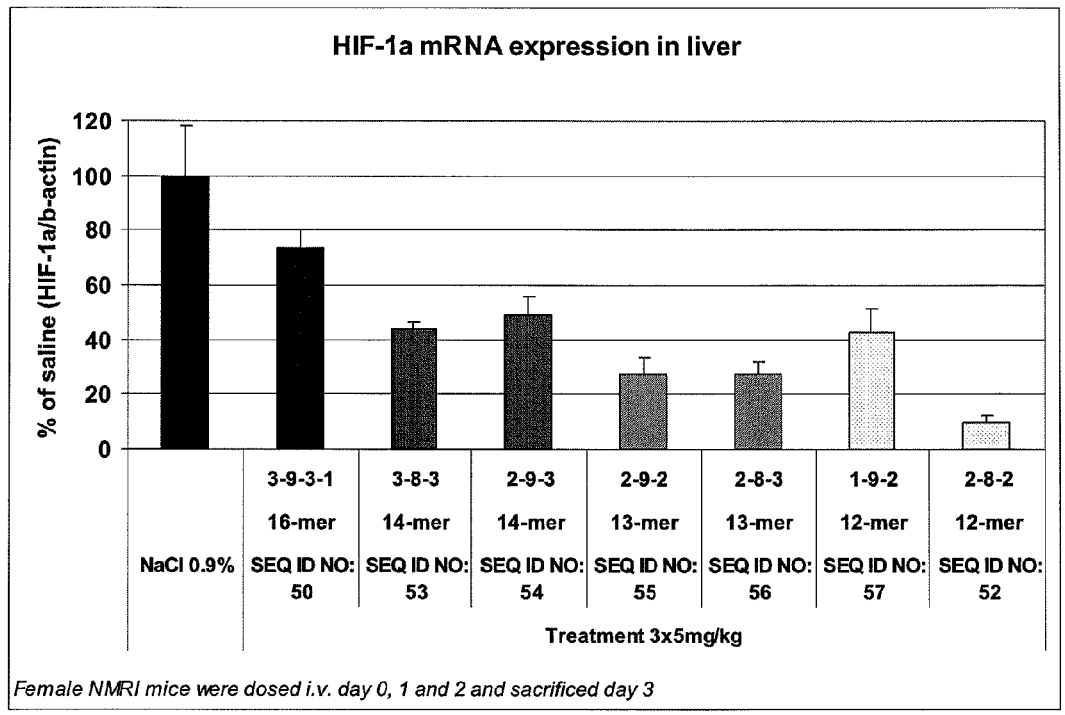
FIG. 13 NMRI mice were dosed 5 mg/kg/dose on 3 consecutive days (one dose/day i.v.) and animals were sacrificed 24 hours after last dosing. At sacrifice, liver tissue were sampled. RNA was isolated from the tissues and the expression of Hif1-alpha mRNA was measured using qPCR.
Figure 14:
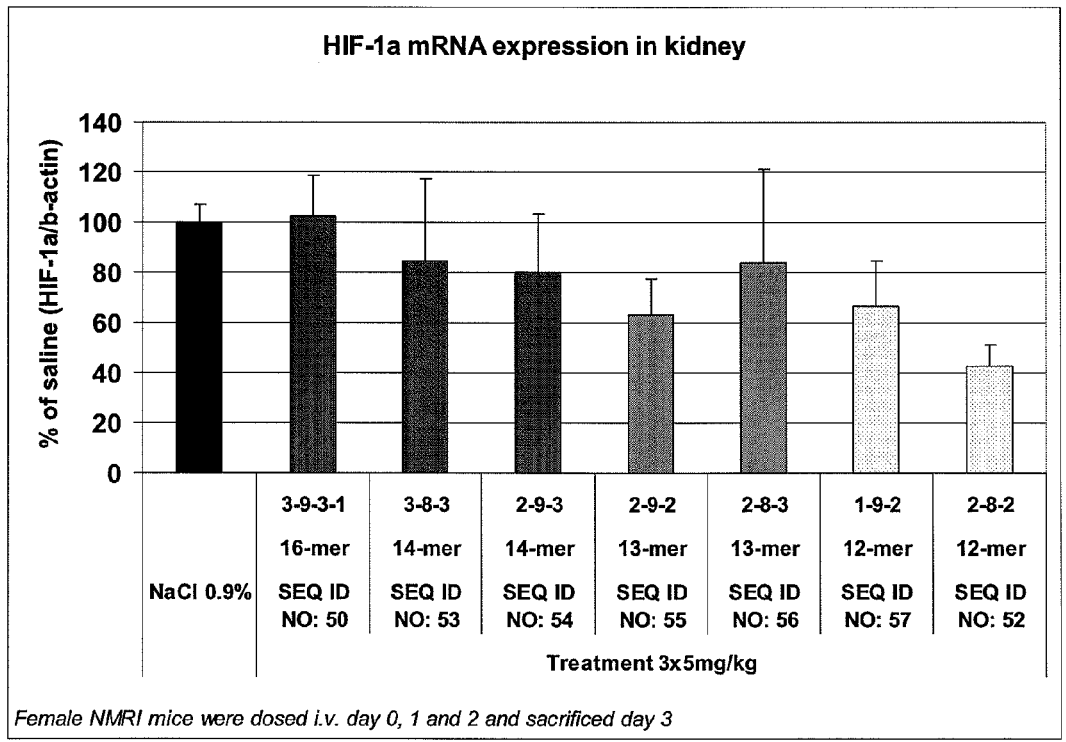
FIG. 14 NMRI mice were dosed 5 mg/kg/dose on 3 consecutive days (one dose/day i.v.) and animals were sacrificed 24 hours after last dosing. At sacrifice, kidney tissue were sampled. RNA was isolated from the tissues and the expression of Hif1-alpha mRNA was measured using qPCR.

Different Length (16-mer-12mer) of Oligonucleotides Targeting Hif1-Alpha mRNA (Dosing 3*5 mg/kg i.v. Three Consecutive Days) in Liver and Kidney In this study 5 mg/kg/dose were dosed to NMRI mice on 3 consecutive days (one dose/day i.v.) and animals were sacrificed 24 hours after last dosing. At sacrifice, liver and kidney tissue were sampled. RNA was isolated from the tissues and the expression of Hif1-alpha mRNA was measured using qPCR.
SEQ ID NOS 50, 53, 54, 55, 56, 57, 52 against Hif1-alpha down-regulated Hif1-alpha mRNA by 25%, 55%, 50%, 70%, 70% 58% and 90% respectively in the liver and down-regulated Hif1-alpha mRNA in kidney by 0%, 15%, 20%, 40%, 20%, 30% and 60% respectively. (FIGS. 13 and 14)

Example 12

Figure 15:
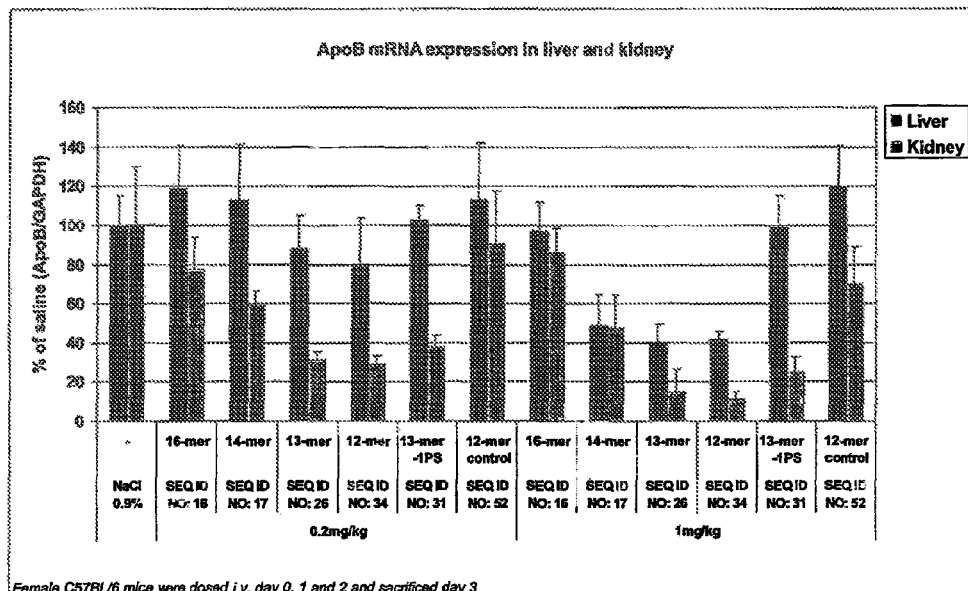
FIG. 15 Female C57BL/6 mice were dosed with either 0.2 mg/kg or 1 mg/kg on 3 consecutive days (one dose/day i.v.) and animals were sacrificed 24 hours after last dosing. At sacrifice, liver and kidney tissue were sampled. RNA was isolated from the tissues and the expression of ApoB mRNA was measured using qPCR.
Figure 16:
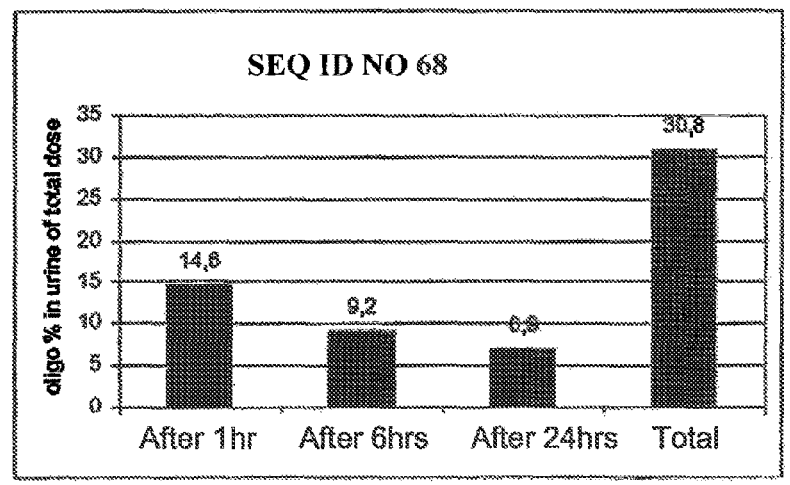
FIG. 16: The amount of oligomer SEQ ID NO 68 present in the urine of mouse injected with 1×50 mg/kg at 1 hr, 6 hr, and 24 hrs after injection, and the total amount.
Figure 17:
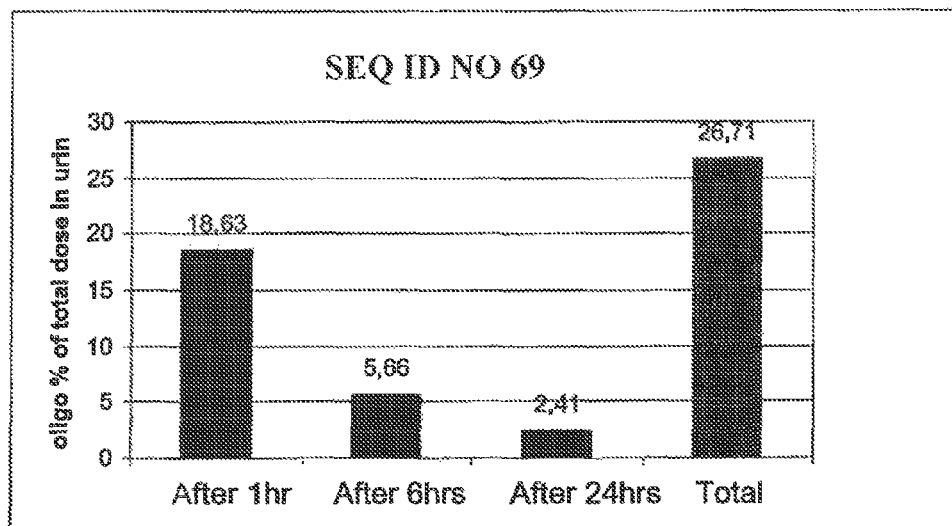
FIG. 17: The amount of oligomer SEQ ID NO 69 present in the urine of mouse injected with 1×50 mg/kg at 1 hr, 6 hr, and 24 hrs after injection, and the total amount.
Figure 18:
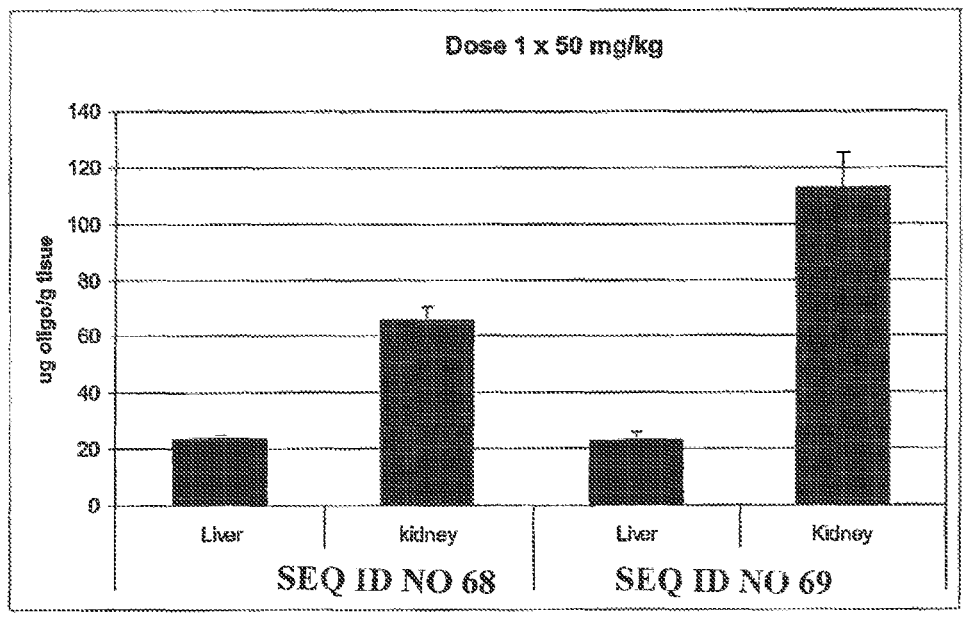
FIG. 18: The amount of oligomers SEQ ID NO 68 and SEQ ID NO 69 present in the liver and kidney of mice injected with 1×50 mg/kg at 24 hrs after injection.
Figure 19:
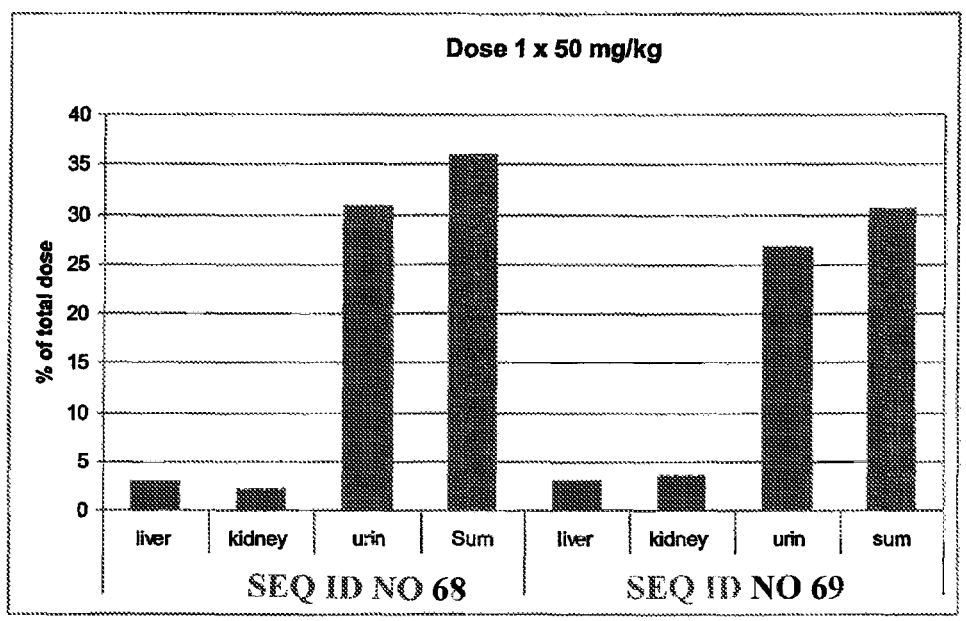
FIG. 19: Biodistribution/bioavailability of oligomers SEQ ID NO 68 and SEQ ID NO 69 present in the liver, kidney, urine and other tissues of mice injected with 1×50 mg/kg at 24 hrs after injection.

ApoB mRNA Knockdown in Liver and Kidney. Shifting the ApoB mRNA Knockdown from Liver to Kidney In this study Female C57BL/6 mice were dosed with either 0.2 mg/kg or 1 mg/kg on 3 consecutive days (one dose/day i.v.) and animals were sacrificed 24 hours after last dosing. At sacrifice, liver and kidney tissue were sampled. RNA was isolated from the tissues and the expression of ApoB mRNA was measured using qPCR.
SEQ ID NOS 16, 17, 26, 34, 31, against ApoB mRNA and SEQ ID NO 52 against Hif1-alpha were monitored for their ability to downregulate ApoB mRNA in liver and kidney. (FIG. 15). SEQ ID NOS 16, 17, 26, 34, 31, 52 downregulate ApoB mRNA in liver/kidney 0%/20%, 0%/40%, 10%/70%, 20%/70%, 0%/65%, 0%/0% respectively at 0.2 mg/kg and 0%/5%, 50%/50%, 60%/85%, 60%/90%, 0%/80%, 0%/30% respectively at 1.0 mg/kg. In SEQ ID NO 31 one phosphorthioate has been replaced by a phosphodiester at linkaged 12 from the 5' end. This modification directs the downregulation of ApoB mRNA with SEQ ID NO 31 towards the kidney (FIG. 15).

Example 13

Comparison of Biodistribution of Fully Phosphorothioate Gapmer with Equivalent Oligomer where Two Phosphorothioate Linkages have been Replaced with Phosphodiester The following oligomers were synthesised:

| Test substance | | Target Sequence |
|---|---|---|
| SEQ ID NO 67 | Hif-1α | TGGCAAGCATCCTGTA (Motif sequence) |
| SEQ ID NO 68 | Hif-1α | 5'-$T_s$°$G_s$°$G_s$°$c_s a_s a_s g_s c_s a_s t_s c_s c_s T_s$°$G_s$°$T_s$°a-3' |
| SEQ ID NO 69 | Hif-1α | 5'-$T_s$°$G$°$G_s$°$c_s a_s a_s g_s c_s a_s t_s c_s c T_s$°$G_s$°$T_s$°a-3' |

The oligomers were injected into mice at a dosage of 50 mg/kg. Urine was sampled after 1 hour, 6 hours and 24 hours. Animals were killed after 24 hours, and the levels of each oligomer present in the liver and kidney was assessed.

The results are shown in FIGS. 16, 17, 18 and 19.

SEQ ID NO 68 was found to be secreted at a slightly higher rate from the urine over the 24 hour period, although the initial rate of excretion appears to be higher with SEQ ID NO 69.

The amount of SEQ ID NO 69 with 2 PO's distributed to the kidney is almost twice as much as SEQ ID NO 68.

SEQ ID NO 69 shows a wider biodistribution to other tissues—69% of SEQ ID NO 69 distributes to other tissues compared to 64% of SEQ ID NO 68.

The invention claimed is:

1. An oligomer 10-14 nucleobase units in length, wherein the nucleobase sequence of said oligomer comprises the formula (5'-3'), AB-C, wherein:
region A (5' region) comprises 1-3 contiguous locked nucleic acid (LNA) nucleobase units;
region B (central domain) comprises 7-9 contiguous nucleobase units and is capable of recruiting RNase H when formed in a duplex with a complementary RNA molecule; and
region C (3' region) comprises 1-3 contiguous locked nucleic acid (LNA) nucleobase units;
and wherein 1, 2 or 3 internucleoside linkages adjacent to an LNA unit in region A, region C, or in each of regions A and C are phosphodiester linkages; and wherein the remaining internucleoside linkages are phosphorothioate linkages.

2. The oligomer according to claim 1, wherein region A comprises a phosphodiester linkage between two LNA units.

3. The oligomer according to claim 1, wherein region C comprises a phosphodiester linkage between two LNA units.

4. The oligomer according to claim 1, wherein the number of nucleobases in regions A, B, and C (A-B-C) is selected from the group consisting of: 1-8-2, 2-8-1, 2-8-2, 3-8-3, 2-8-3, and 3-8-2.

5. A conjugate comprising the oligomer of claim 1 and at least one non-nucleotide or non-polynucleotide moiety covalently attached to said oligomer.

6. A pharmaceutical composition comprising the oligomer of claim 1 and a pharmaceutically acceptable diluent, carrier, salt or adjuvant.

7. The oligomer of claim 1, wherein said nucleobase sequence further comprises one or two DNA units (region D), wherein said region D precedes region A.

8. A pharmaceutical composition comprising the conjugate of claim 5 and a pharmaceutically acceptable diluent, carrier, salt, or adjuvant.

9. The oligomer of claim 1, wherein a phosphodiester linkage is present between a LNA unit located at the 3' terminus of region A and the nucleobase unit located at the 5' terminus of region B.

10. The oligomer of claim 1 wherein a phosphodiester linkage is present between a LNA unit located at the 5' terminus of region C and the nucleobase unit located at the 3' terminus of region B.

11. The oligomer according to claim 1, wherein region B consists of nucleobase units selected from the group consisting of DNA units, alpha-L-Oxy LNA units and mixtures thereof.

12. The oligomer according to claim 1, wherein region B consists of DNA units.

13. The oligomer according to claim 4, wherein the number of nucleobases in regions A, B, and C (A-B-C) is 3-8-3.

14. A method for reducing the cellular concentration of an mRNA in a mammalian cell comprising contacting the oligomer of claim 1 with the mammalian cell, wherein said mammalian cell comprises an mRNA species having a nucleobase sequence complementary to said oligomer.

15. The method of claim 14, wherein the cell is a kidney cell.

16. A method for reducing the cellular concentration of an mRNA in a mammalian cell comprising contacting the conjugate of claim 5 with the mammalian cell, wherein said mammalian cell comprises an mRNA species having a nucleobase sequence complementary to the oligomer of the conjugate.

17. The method of claim 16, wherein the cell is a kidney cell.

* * * * *